(12) United States Patent
Strother et al.

(10) Patent No.: US 9,480,846 B2
(45) Date of Patent: *Nov. 1, 2016

(54) SYSTEMS AND METHODS FOR PATIENT CONTROL OF STIMULATION SYSTEMS

(75) Inventors: Robert B. Strother, Willoughby Hills, OH (US); James E. Barber, Avon, OH (US); Joseph J. Mrva, Euclid, OH (US); Christopher A. Thierfelder, Minneapolis, MN (US); Maria E. Bennett, Lyndhurst, OH (US); Geoffrey B. Thrope, Shaker Heights, OH (US); Danny R. Pack, Avon Lake, OH (US); Stuart F. Rubin, Orange Village, OH (US)

(73) Assignee: Medtronic Urinary Solutions, Inc., Minneapolis, MN (US)

( * ) Notice: Subject to any disclaimer, the term of this patent is extended or adjusted under 35 U.S.C. 154(b) by 801 days.

This patent is subject to a terminal disclaimer.

(21) Appl. No.: 11/712,379

(22) Filed: Feb. 28, 2007

(65) Prior Publication Data

US 2007/0270921 A1    Nov. 22, 2007

Related U.S. Application Data

(63) Continuation-in-part of application No. 11/516,890, filed on Sep. 7, 2006, now abandoned.

(60) Provisional application No. 60/801,003, filed on May 17, 2006.

(51) Int. Cl.
*A61N 1/378* (2006.01)
*A61N 1/372* (2006.01)
(Continued)

(52) U.S. Cl.
CPC ............ *A61N 1/37235* (2013.01); *A61N 1/08* (2013.01); *A61N 1/3787* (2013.01); *A61N 1/3605* (2013.01); *A61N 1/37223* (2013.01); *A61N 1/37247* (2013.01); *A61N 1/37264* (2013.01)

(58) Field of Classification Search
CPC .................... A61N 1/37235; A61N 1/3787
USPC ....................................................... 607/59–61
See application file for complete search history.

(56) References Cited

U.S. PATENT DOCUMENTS 3,421,511 A    1/1969    Schwartz et al.
3,654,933 A    4/1972    Hagfors
(Continued)

FOREIGN PATENT DOCUMENTS

CA       2121219      10/1995
WO    WO00/19939     4/2000
(Continued)

OTHER PUBLICATIONS

Mar. 2002 Physician's Manual: Cyberonics Model 201 NeuroCybernetic Prosthesis (NCP) Programming Wand, pp. 1-18.
(Continued)

*Primary Examiner* — Eric D. Bertram
(74) *Attorney, Agent, or Firm* — Shumaker & Sieffert, P.A.

(57) ABSTRACT

Provided is a portable controller and associated method that provides a patient or caregiver the ability to recharge and alter the parameters of an implanted medical device, while allowing the patient substantially unobstructed mobility. To enable mobility, the controller may be worn on a belt or clothing. The controller also allows the patient to turn device stimulation on and off, check battery status, and to vary stimulation parameters within ranges that may be predefined and programmed by a clinician. The controller communicates with the medical device to retrieve information and make parameter adjustments using wireless telemetry, and it can send and receive information from several feet away from the implanted medical device. Charging of a battery contained in the implanted medical device is achieved via an inductive radio frequency link using a charge coil placed in close proximity to the medical device.

36 Claims, 11 Drawing Sheets

(51) Int. Cl.
*A61N 1/08* (2006.01)
*A61N 1/36* (2006.01)

(56) References Cited

U.S. PATENT DOCUMENTS

| | | | |
|---|---|---|---|
| 3,727,616 A | 4/1973 | Lenzkes |
| 3,774,618 A | 11/1973 | Avery |
| 3,870,051 A | 3/1975 | Brindley |
| 3,902,501 A | 9/1975 | Citron et al. |
| 3,926,198 A | 12/1975 | Kolenik |
| 3,939,841 A | 2/1976 | Dohring et al. |
| 3,939,843 A | 2/1976 | Smyth |
| 3,941,136 A | 3/1976 | Bucalo |
| 3,943,932 A | 3/1976 | Woo |
| 3,943,938 A | 3/1976 | Wexler |
| 4,232,679 A | 11/1980 | Schulman |
| 4,254,775 A | 3/1981 | Langer |
| 4,257,423 A | 3/1981 | McDonald |
| 4,262,678 A | 4/1981 | Stokes |
| 4,398,545 A | 8/1983 | Wilson |
| 4,406,288 A | 9/1983 | Horwinski et al. |
| 4,407,303 A | 10/1983 | Akerstrom |
| 4,512,351 A | 4/1985 | Pohndorf |
| 4,519,404 A | 5/1985 | Fleischhacker |
| 4,569,351 A | 2/1986 | Tang |
| 4,573,481 A | 3/1986 | Bullara |
| 4,585,005 A | 4/1986 | Lue et al. |
| 4,585,013 A | 4/1986 | Harris |
| 4,590,689 A | 5/1986 | Rosenberg |
| 4,590,946 A | 5/1986 | Loeb |
| 4,592,360 A | 6/1986 | Lesnick |
| 4,602,624 A | 7/1986 | Naples et al. |
| 4,607,639 A | 8/1986 | Tanagho et al. |
| 4,628,942 A | 12/1986 | Sweeney et al. |
| 4,649,936 A | 3/1987 | Ungar et al. |
| 4,658,515 A | 4/1987 | Oatman |
| 4,703,755 A | 11/1987 | Tanagho et al. |
| 4,716,888 A | 1/1988 | Wesner |
| 4,721,118 A | 1/1988 | Harris |
| 4,739,764 A | 4/1988 | Lue et al. |
| 4,741,341 A | 5/1988 | Marach |
| 4,750,499 A | 6/1988 | Hoffer |
| 4,771,779 A | 9/1988 | Tanagho et al. |
| 4,793,353 A | 12/1988 | Borkan |
| 4,835,372 A | 5/1989 | Gombrich et al. |
| 4,920,979 A | 5/1990 | Bullara |
| 4,926,875 A | 5/1990 | Rabinovitz et al. |
| 4,934,368 A | 6/1990 | Lynch |
| 4,940,065 A | 7/1990 | Tanagho et al. |
| 4,989,617 A | 2/1991 | Memberg et al. |
| 5,095,905 A | 3/1992 | Klepinski |
| 5,113,869 A | 5/1992 | Nappholz et al. |
| 5,154,172 A | 10/1992 | Terry, Jr. et al. |
| 5,215,086 A | 6/1993 | Terry, Jr. et al. |
| 5,222,494 A | 6/1993 | Baker, Jr. |
| D337,820 S | 7/1993 | Hooper et al. |
| 5,235,980 A | 8/1993 | Varrichio et al. |
| 5,257,634 A | 11/1993 | Kroll |
| 5,265,608 A | 11/1993 | Lee et al. |
| 5,282,845 A | 2/1994 | Bush et al. |
| 5,289,821 A | 3/1994 | Swartz |
| 5,300,107 A | 4/1994 | Stokes et al. |
| 5,324,322 A | 6/1994 | Grill, Jr. et al. |
| 5,330,515 A | 7/1994 | Rutecki et al. |
| 5,335,664 A | 8/1994 | Nagashima |
| 5,344,439 A | 9/1994 | Otten |
| 5,369,257 A | 11/1994 | Gibbon |
| 5,370,671 A | 12/1994 | Maurer et al. |
| 5,397,338 A | 3/1995 | Grey et al. |
| 5,400,784 A | 3/1995 | Durand et al. |
| 5,411,537 A | 5/1995 | Munshi et al. |
| 5,449,378 A | 9/1995 | Schouenborg |
| 5,454,840 A | 10/1995 | Krakovsky et al. |
| 5,461,256 A | 10/1995 | Yamada |
| 5,476,500 A | 12/1995 | Fain et al. |
| 5,480,416 A | 1/1996 | Garcia et al. |
| 5,486,202 A | 1/1996 | Bradshaw |
| 5,487,756 A | 1/1996 | Kallesoe et al. |
| 5,505,201 A | 4/1996 | Grill, Jr. et al. |
| 5,531,778 A | 7/1996 | Maschino et al. |
| 5,540,730 A | 7/1996 | Terry, Jr. et al. |
| 5,562,717 A | 10/1996 | Tippey et al. |
| 5,588,960 A | 12/1996 | Edwards et al. |
| 5,607,461 A | 3/1997 | Lathrop |
| 5,634,462 A | 6/1997 | Tyler et al. |
| 5,645,586 A | 7/1997 | Meltzer |
| 5,669,161 A | 9/1997 | Huang |
| 5,683,432 A | 11/1997 | Goedeke et al. |
| 5,683,447 A | 11/1997 | Bush et al. |
| 5,690,693 A | 11/1997 | Wang et al. |
| 5,702,431 A * | 12/1997 | Wang et al. .................. 607/61 |
| 5,713,939 A | 2/1998 | Nedungadi et al. |
| 5,716,384 A | 2/1998 | Snell |
| 5,722,482 A | 3/1998 | Buckley |
| 5,722,999 A | 3/1998 | Snell |
| 5,733,313 A * | 3/1998 | Barreras et al. ............. 607/33 |
| 5,733,322 A | 3/1998 | Starkebaum |
| 5,741,313 A | 4/1998 | Davis et al. |
| 5,741,319 A | 4/1998 | Woloszko et al. |
| 5,752,977 A | 5/1998 | Grevious et al. |
| 5,755,767 A | 5/1998 | Doan et al. |
| 5,759,199 A | 6/1998 | Snell |
| 5,807,397 A | 9/1998 | Barreras |
| 5,824,027 A | 10/1998 | Hoffer et al. |
| 5,843,141 A | 12/1998 | Bischoff et al. |
| 5,857,968 A | 1/1999 | Benja-Athon |
| 5,861,015 A | 1/1999 | Benja-Athon |
| 5,861,016 A | 1/1999 | Swing |
| 5,899,933 A | 5/1999 | Bhadra et al. |
| 5,919,220 A | 7/1999 | Stieglitz et al. |
| 5,922,015 A | 7/1999 | Schaldach |
| 5,938,596 A | 8/1999 | Woloszko et al. |
| 5,948,006 A | 9/1999 | Mann |
| 5,957,951 A | 9/1999 | Cazaux et al. |
| 5,984,854 A | 11/1999 | Ishikawa et al. |
| 6,004,662 A | 12/1999 | Buckley |
| 6,016,451 A | 1/2000 | Sanchez-Rodarte |
| 6,026,328 A | 2/2000 | Peckham et al. |
| 6,055,456 A | 4/2000 | Gerber |
| 6,055,457 A | 4/2000 | Bonner |
| 6,061,596 A | 5/2000 | Richmond et al. |
| 6,091,995 A | 7/2000 | Ingle et al. |
| 6,125,645 A | 10/2000 | Horn |
| 6,126,611 A | 10/2000 | Bourgeois et al. |
| 6,166,518 A * | 12/2000 | Echarri et al. ................ 320/106 |
| 6,169,925 B1 | 1/2001 | Villaseca et al. |
| 6,181,965 B1 | 1/2001 | Loeb et al. |
| 6,181,973 B1 | 1/2001 | Ceron et al. |
| 6,185,452 B1 | 2/2001 | Schulman et al. |
| 6,200,265 B1 | 3/2001 | Walsh et al. |
| 6,208,894 B1 | 3/2001 | Schulman et al. |
| 6,212,431 B1 | 4/2001 | Hahn et al. |
| 6,216,038 B1 | 4/2001 | Hartlaub et al. |
| 6,240,316 B1 | 5/2001 | Richmond et al. |
| 6,240,317 B1 | 5/2001 | Villaseca et al. |
| 6,249,703 B1 | 6/2001 | Stanton et al. |
| 6,257,906 B1 | 7/2001 | Price et al. |
| 6,266,557 B1 | 7/2001 | Roe et al. |
| 6,275,737 B1 | 8/2001 | Mann |
| 6,292,703 B1 | 9/2001 | Meier et al. |
| 6,308,101 B1 | 10/2001 | Faltys et al. |
| 6,308,105 B1 | 10/2001 | Duysens et al. |
| 6,319,208 B1 | 11/2001 | Abita et al. |
| 6,319,599 B1 | 11/2001 | Buckley |
| 6,321,124 B1 | 11/2001 | Cigaina |
| 6,338,347 B1 | 1/2002 | Chung |
| 6,345,202 B2 | 2/2002 | Richmond et al. |
| 6,360,750 B1 | 3/2002 | Gerber et al. |
| 6,370,433 B1 | 4/2002 | Hartlaub et al. |
| 6,381,496 B1 | 4/2002 | Meadows et al. |
| 6,409,675 B1 | 6/2002 | Turcott |
| 6,432,037 B1 | 8/2002 | Eini et al. |
| 6,442,432 B2 | 8/2002 | Lee |
| 6,442,433 B1 | 8/2002 | Linberg |

(56) References Cited

U.S. PATENT DOCUMENTS

| | | |
|---|---|---|
| 6,445,955 B1 | 9/2002 | Michelson et al. |
| 6,449,512 B1 | 9/2002 | Boveja |
| 6,450,172 B1 | 9/2002 | Hartlaub et al. |
| 6,453,198 B1 | 9/2002 | Torgerson et al. |
| 6,456,866 B1 | 9/2002 | Tyler et al. |
| 6,464,672 B1 | 10/2002 | Buckley |
| 6,482,154 B1 | 11/2002 | Haubrich et al. |
| 6,493,587 B1 | 12/2002 | Eckmiller et al. |
| 6,493,881 B1 | 12/2002 | Picotte |
| 6,505,074 B2 | 1/2003 | Boveja et al. |
| 6,505,077 B1 | 1/2003 | Kast et al. |
| 6,510,347 B2 | 1/2003 | Borkan |
| 6,516,227 B1 | 2/2003 | Meadows et al. |
| 6,535,766 B1 | 3/2003 | Thompson et al. |
| 6,539,253 B2 | 3/2003 | Thompson et al. |
| 6,542,776 B1 | 4/2003 | Gordon et al. |
| 6,553,263 B1 | 4/2003 | Meadows et al. |
| 6,567,703 B1 | 5/2003 | Thompson et al. |
| 6,574,510 B2 | 6/2003 | Von Arx et al. |
| 6,580,947 B1 | 6/2003 | Thompson |
| 6,591,137 B1 | 7/2003 | Fischell et al. |
| 6,597,954 B1 | 7/2003 | Fischell et al. |
| 6,600,956 B2 | 7/2003 | Maschino et al. |
| 6,607,500 B2 | 8/2003 | DaSilva et al. |
| 6,613,953 B1 | 9/2003 | Altura |
| 6,622,037 B2 | 9/2003 | Kasano |
| 6,622,048 B1 | 9/2003 | Mann et al. |
| 6,641,533 B2 * | 11/2003 | Causey et al. ............. 600/300 |
| 6,643,552 B2 | 11/2003 | Edell et al. |
| 6,650,943 B1 | 11/2003 | Whitehurst et al. |
| 6,652,449 B1 | 11/2003 | Gross et al. |
| 6,658,300 B2 | 12/2003 | Govari et al. |
| 6,660,265 B1 | 12/2003 | Chen |
| 6,672,895 B2 | 1/2004 | Scheiner |
| 6,684,109 B1 | 1/2004 | Osypka |
| 6,687,543 B1 | 2/2004 | Isaac |
| 6,701,188 B2 | 3/2004 | Stroebel et al. |
| 6,721,602 B2 | 4/2004 | Engmark et al. |
| 6,735,474 B1 | 5/2004 | Loeb et al. |
| 6,735,475 B1 | 5/2004 | Whitehurst et al. |
| 6,754,538 B2 | 6/2004 | Linberg |
| 6,775,715 B2 | 8/2004 | Spitaels et al. |
| 6,804,558 B2 | 10/2004 | Haller et al. |
| 6,836,684 B1 | 12/2004 | Rijkhoff et al. |
| 6,836,685 B1 | 12/2004 | Fitz |
| 6,845,271 B2 | 1/2005 | Fang et al. |
| 6,850,803 B1 | 2/2005 | Jimenez et al. |
| 6,855,410 B2 | 2/2005 | Buckley |
| 6,856,506 B2 | 2/2005 | Doherty |
| 6,859,364 B2 | 2/2005 | Yuasa et al. |
| 6,862,480 B2 | 3/2005 | Cohen et al. |
| 6,868,288 B2 | 3/2005 | Thompson |
| 6,891,353 B2 | 5/2005 | Tsukamoto |
| 6,893,395 B1 | 5/2005 | Kraus et al. |
| 6,895,280 B2 | 5/2005 | Meadows et al. |
| 6,904,324 B2 | 6/2005 | Bishay |
| 6,907,293 B2 | 6/2005 | Grill et al. |
| 6,907,295 B2 | 6/2005 | Gross et al. |
| 6,920,539 B2 | 7/2005 | Qawami et al. |
| 6,925,330 B2 | 8/2005 | Kleine |
| 6,928,320 B2 | 8/2005 | King |
| 6,931,284 B2 | 8/2005 | Engmark et al. |
| 6,937,894 B1 | 8/2005 | Isaac et al. |
| 6,963,780 B2 | 11/2005 | Ruben et al. |
| 6,974,411 B2 | 12/2005 | Belson |
| 6,990,376 B2 | 1/2006 | Tanagho |
| 6,999,819 B2 | 2/2006 | Swoyer et al. |
| 7,031,768 B2 | 4/2006 | Anderson et al. |
| 7,047,078 B2 | 5/2006 | Boggs, II et al. |
| 7,078,359 B2 | 7/2006 | Stepanian et al. |
| 7,101,607 B2 | 9/2006 | Mollendorf |
| 7,103,923 B2 | 9/2006 | Picotte |
| 7,118,801 B2 | 10/2006 | Ristic-Lehmann |
| 7,136,695 B2 | 11/2006 | Pless |
| 7,167,756 B1 | 1/2007 | Torgerson et al. |
| 7,177,690 B2 | 2/2007 | Woods et al. |
| 7,177,698 B2 | 2/2007 | Klosterman et al. |
| 7,187,968 B2 | 3/2007 | Wolf |
| 7,187,983 B2 | 3/2007 | Dahlberg et al. |
| 7,191,012 B2 | 3/2007 | Boveja |
| 7,198,603 B2 | 4/2007 | Penner et al. |
| 7,225,032 B2 | 5/2007 | Schmeling et al. |
| 7,239,918 B2 | 7/2007 | Strother et al. |
| 7,254,448 B2 | 8/2007 | Almendinger et al. |
| 7,269,457 B2 | 9/2007 | Shafer et al. |
| 7,280,872 B1 | 10/2007 | Mosesov et al. |
| 7,317,947 B2 | 1/2008 | Wahlstrand |
| 7,328,068 B2 | 2/2008 | Spinelli et al. |
| 7,342,793 B2 | 3/2008 | Ristic-Lehmann |
| 7,343,202 B2 | 3/2008 | Mrva et al. |
| 7,369,897 B2 | 5/2008 | Boveja |
| 7,376,467 B2 | 5/2008 | Thrope |
| 7,475,245 B1 | 1/2009 | Healy et al. |
| 7,499,758 B2 | 3/2009 | Cates |
| 7,565,198 B2 | 7/2009 | Bennett |
| 8,195,304 B2 * | 6/2012 | Strother ............. A61B 5/0031 607/60 |
| 2001/0022719 A1 | 9/2001 | Armitage et al. |
| 2002/0007198 A1 | 1/2002 | Haupert et al. |
| 2002/0019652 A1 | 2/2002 | Da Silva et al. |
| 2002/0026224 A1 | 2/2002 | Thompson et al. |
| 2002/0055761 A1 | 5/2002 | Mann et al. |
| 2002/0055779 A1 | 5/2002 | Andrews |
| 2002/0077572 A1 | 6/2002 | Fang et al. |
| 2002/0109621 A1 | 8/2002 | Khair et al. |
| 2002/0123672 A1 | 9/2002 | Christophersom et al. |
| 2002/0161403 A1 | 10/2002 | Meadows et al. |
| 2002/0164474 A1 | 11/2002 | Buckley |
| 2003/0018365 A1 | 1/2003 | Loeb |
| 2003/0065368 A1 | 4/2003 | VanDerHoeven |
| 2003/0074030 A1 | 4/2003 | Leyde et al. |
| 2003/0078633 A1 | 4/2003 | Firlik et al. |
| 2003/0088295 A1 | 5/2003 | Cox |
| 2003/0100930 A1 | 5/2003 | Cohen et al. |
| 2003/0114897 A1 | 6/2003 | Von Arx et al. |
| 2003/0114898 A1 | 6/2003 | Von Arx et al. |
| 2003/0114905 A1 | 6/2003 | Kuzma |
| 2003/0120259 A1 | 6/2003 | Mickley |
| 2003/0139783 A1 | 7/2003 | Kilgore et al. |
| 2003/0149459 A1 | 8/2003 | Von Arx et al. |
| 2003/0220673 A1 | 11/2003 | Snell |
| 2004/0030360 A1 | 2/2004 | Eini et al. |
| 2004/0059392 A1 | 3/2004 | Parramon et al. |
| 2004/0082977 A1 | 4/2004 | Engmark et al. |
| 2004/0088024 A1 | 5/2004 | Firlik et al. |
| 2004/0093093 A1 | 5/2004 | Andrews |
| 2004/0098068 A1 | 5/2004 | Carbunaru et al. |
| 2004/0147886 A1 | 7/2004 | Bonni |
| 2004/0150963 A1 | 8/2004 | Holmberg |
| 2004/0204744 A1 | 10/2004 | Penner et al. |
| 2004/0209061 A1 | 10/2004 | Farnworth |
| 2005/0004619 A1 | 1/2005 | Wahlstrand et al. |
| 2005/0038491 A1 | 2/2005 | Haack |
| 2005/0055063 A1 | 3/2005 | Loeb et al. |
| 2005/0080463 A1 | 4/2005 | Stahmann |
| 2005/0107841 A1 | 5/2005 | Meadows et al. |
| 2005/0131493 A1 | 6/2005 | Boveja et al. |
| 2005/0143787 A1 | 6/2005 | Boveja et al. |
| 2005/0149146 A1 | 7/2005 | Boveja et al. |
| 2005/0175799 A1 | 8/2005 | Farnworth |
| 2005/0192526 A1 | 9/2005 | Biggs et al. |
| 2005/0277844 A1 | 12/2005 | Strother et al. |
| 2005/0277999 A1 | 12/2005 | Strother et al. |
| 2005/0278000 A1 | 12/2005 | Strother et al. |
| 2006/0004421 A1 | 1/2006 | Bennett et al. |
| 2006/0025829 A1 | 2/2006 | Armstrong et al. |
| 2006/0033720 A1 | 2/2006 | Robbins et al. |
| 2006/0035054 A1 | 2/2006 | Stepanian et al. |
| 2006/0085039 A1 | 4/2006 | Hastings et al. |
| 2006/0100673 A1 | 5/2006 | Koinzer |
| 2006/0113955 A1 | 6/2006 | Nunally |
| 2006/0122660 A1 | 6/2006 | Boveja et al. |
| 2006/0173507 A1 | 8/2006 | Mrva et al. |
| 2006/0184208 A1 | 8/2006 | Boggs et al. |

(56) References Cited

U.S. PATENT DOCUMENTS

| | | |
|---|---|---|
| 2006/0271112 A1 | 11/2006 | Martinson et al. |
| 2007/0060967 A1 | 3/2007 | Strother et al. |
| 2007/0060980 A1 | 3/2007 | Strother et al. |
| 2007/0100411 A1 | 5/2007 | Bonde |
| 2007/0123952 A1 | 5/2007 | Strother |
| 2007/0239224 A1 | 10/2007 | Bennett et al. |
| 2008/0071322 A1 | 3/2008 | Mrva et al. |
| 2008/0097564 A1 | 4/2008 | Lathrop |
| 2008/0132969 A1 | 6/2008 | Bennett et al. |

FOREIGN PATENT DOCUMENTS

| | | |
|---|---|---|
| WO | WO 01/83029 A1 | 11/2001 |
| WO | WO03/092227 | 4/2003 |
| WO | WO2006/055547 | 5/2006 |
| WO | WO 2006055547 A2 * | 5/2006 |
| WO | WO2009/058984 | 5/2009 |

OTHER PUBLICATIONS

Aug. 2002 Physician's Manual: Cyberonics Models 100 and 101 NeuroCybernetic Prosthesis System, NCP Pulse Generator, pp. 1-92.

2005 Advanced Neuromodulation Systems, Inc., ANS Medical—Determining chronic pain causes and treatments; website: http://www.ans-meeical.com/medicalprofessional/physician/rechargeableipgsystems.cfm.

2004 Advanced Bionics Corporation Summary of Safety and Effectiveness, pp. 1-18.

2004 Advanced Bionics Corporation Physician Implant Manual.

2005 Cyberonics VNS Therapy website: http://www.vnstherapy.com/Epilepsy/hcp/forsurgeons/implantedcomponents.aspx.

2004 Advanced Bionics Corporation Patient System Handbook.

Oct. 2001 Advanced Neurostimulation Systems, Inc. ANS Genesis Neurosimulation System Programmer User's Guide.

Nov. 21, 2001 Advanced Neuromodulation Systems, Inc. (ANS) Summary of Safety and Effectivenss Data, pp. 1-17.

Notification of Transmittal of the International Search Report and the Written Opinion of the International Searching Authority, or the Declaration dated Jul. 18, 2008 for corresponding PCT Application No. PCT/US2008/002540 (10 pgs.).

U.S. Appl. No. 11/516,890, filed Sep. 7, 2006 by Strothers et al, entitled: Implantable Pulse Generator Systems and Methods for Providing Functional and/or Therapeutic Stimulation of Muscles and/or Nerves and/or central nervous system tissue.

U.S. Appl. No. 60/486,573, filed Jul. 11, 2003, Loeb et al.

A Breakthrough in Advanced Materials, Aspen Aerogels, Inc. (1 pg) www.aerogels.com, 2003.

Bemelmans, Bart L.H., et al., "Neuromodulation by Implant for Treating Lower Urinary Tract Symptoms and Dysfunction," Eur. Urol. Aug. 1999 36(2): 81-91.

Bower, W.F., et al., "A Urodynamic Study of Surface Neuromodulation versus Sham in Detrusor Instability and Sensory Urgency", J. Urology 1998; 160: 2133-2136.

Brindley, G., et al., "Sacral Anterior Root Stimulators for Bladder Control in Paraplegia", Paraplegia 1982; 20(6):365-381.

Caldwell, C. (1971) Multielectrode Electrical Stimulation of Nerve, in Development of Orthotic Systems using Functional Electrical Stimulation and Myoelectric Control, Final Report Project #19-P-58391-F-01, University of Lublinana, Faculty of Electrical Engineering, Lubjiana, Yugoslavia.

Corbett, Scott S., http://crisp.cit.nih.gov/ Abstract, High-Density Liquid Crystal Polymer Cochlear Electrodes, downloaded Sep. 18, 2006.

Craggs, M., and McFarlane, J.P., "Neuromodulation of the Lower Urinary Tract," Experimental Physiology, 84, 149-160 1999.

Crampon et al., "Nerve Cuff Electrode with Shape Memory Alloy Armature: Design and Fabrication", Bio-Medical Materials and Engineering 12 (2002) 397-410.

Craggs, M., et al., "Aberrant reflexes and function of the pelvic organs following spinal cord injury in man", Autonomic Neuroscience: Basic & Clinical, 126-127 (2006), 355-370.

Crampon et al., "New Easy to Install Nerve Cuff Electrode Using Shape Memory Alloy Armature", Artificial Organs, 23(5):392-395, 1999.

Dalmose, A.L., et al., "Conditional Stimulation of the Dorsal Penile/Clitoral Nerve", Neurourol Urodyn 2003; 22(2):130-137.

Edell, David J., PhD, Boston Healthcare Research Device, Feb. 15, 2006.

Fossberg, E., et al. "Maximal Electrical Stimulation in the Treatment of Unstable Detrusor and Urge Incontinence", Eur Urol 1990; 18:120-123.

Grill, et al., "Emerging clinical applications of electrical stimulation: opportunities for restoration of function", Journal of Rehabilitation Research and Development, vol. 38, No. 6, Nov./Dec. 2001.

Grill, W. M., Mortimer, J.T., (1996) Quantification of recruitment properties of multiple contact cuff electrodes, IEEE Transactions on Rehabilitation Engineering 4(2):49-62.

Grill, W.M., (2001) "Selective Activation of the Nervous System for Motor System Neural Prosthesis" in Intelligent Systems and Technologies in Rehabilitation Engineering, H-N.L. Teodorescu, L. C. Jain, Eds., CRC Press, pp. 211-241.

Gustafson, K., et al. "A Urethral Afferent Mediated Excitatory Bladder Reflex Exists in Humans", Neurosci Lett 2004: 360(1-2):9-12.

Gustafson, K., et al., "A Catheter Based Method to Activate Urethral Sensory Nerve Fibers", J Urol 2003: 170(1):126-129.

Jezernik, S., "Electrical Stimulation for the Treatment of Bladder Dysfunction: Current Status and Future Possibilities", Neurol. Res. 2002: 24:413-30.

Jezernik, S., et al., "Detection and inhibition of hyper-reflexia-like bladder contractions in the cat by sacral nerve root recording and electrical stimulation," Neurourology and Urodynamics, 20(2), 215-230 (2001).

Jiang, C., et al., "Prolonged Increase in Micturition Threshold Volume by Anogenital Afferent Stimulation in the Rat", Br J. Urol. 1998: 82(3):398-403.

Jiang, C-H., et al., "Prolonged enhancement of the micturition reflex in the cat by repetitive stimulation of bladder afferents," Journal of Physiology, 517.2 599-605 (1999).

Juenemann, K., et al., Clinical Significance of Sacral and Pudendal Nerve Anatomy:, J. Urol. 1988; 139(1):74-80.

Lee, Y.H., et al., "Self-Controlled dorsal penile nerve stimulation to inhibit bladder hyperreflexia in incomplete spinal injury: A case report," Arch Phys Med Rehabil., 83, 273-7 (2002).

Loeb et al., "Cuff Electrodes for Chronic Stimulation and Recording of Peripheral Nerve Activity", Journal of Neuroscience Methods, 64 (1996), 95-103.

Madersbacher, H., Urinary Urge and Reflex Incontinence:, Urologe A. 1991: 30(4): 215-222 (Abstract only, article in German).

Mazieres, L., et al., "Bladder Parasympathetic Response to Electrical Stimulation of Urethral Afferents in the Cat", Neurol Urodynam 1997; 16:471-472.

Mazieres, L., et al., "The C Fibre Reflex of the Cat Urinary Bladder", J. Physiol 1998; 513 (Pt 2):531-541.

McNeal, D.R., (1974) Selective Stimulation, in Annual Reports of Progress, Rehabilitation Engineering Center, Ranchio Los Amigos Hospital, Downey, CA, pp. 24-25.

McNeal, D.R., Bowman, B.R., (1985) Selective activation of muscles using peripheral nerve electrodes. Med. and Biol. Eng. and Comp., 23:249-253.

Modern Plastics Worldwide, Notables: 10 Waves of the Future by Modern Plastics Editorial Staff, Sample Molding in Progress: Sep. 1, 2005.

Nakamura, M., et al., "Bladder Inhibition by Penile Electrical Stimulation", Br J Urol 1984: 56:413-415.

Naples, et al., "A Spiral Nerve Cuff Electrode for Peripheral Nerve Stimulation", IEEE Transactions on Biomedical Engineering, vol. 35, No. 11, Nov. 1988.

NeuroControl Corp., NeuroControl StiM System brochure.

(56) References Cited

OTHER PUBLICATIONS

NeuroControl Corp., The NeuroControl StiM System, "World's First Miniturized Multi-Channel Programmable Neuromuscular Stimulator" brochure.
Nissenkorn, Israel, and De Jong, Peter R., 2005 Biocontrol Medical Article: "Lower Urinary Tract," pp. 1253-1258.
Oliver, S., et al., "Measuring the Sensations of Urge and Bladder Filling During Cystometry in Urge Incontinence and the Effects of Neuromodulation", Neurourol Urodyn 2003: 22:7-16.
Previnaire, J.G., "Short-Term Effect of Pudendal Nerve Electrical Stimulation on Detrusor Hyperreflexia in Spinal Cord Injury Patients: Importance of Current Strength", Paraplegia 1996: 34:95-99.
Rijkhoff, N., et al., "Urinary Bladder Control by Electrical Stimulation: Review of Electrical Stimulation Techniques in Spinal Cord Injury", Neurourol Urodyn 1997; 16(1):39-53.
Riley, George A., PhD, www.flipchips.com, Advanced Packaging—Water Level Hermetic Cavity Packaging, originally published in Advanced Packaging Magazine, May 2004.
Riley, George A., PhD, www.flipchips.com, Tutorial 31—Jun. 2003, A survey of Water Level Hermetic Cavity Chip Scale Packages for RF Applications.
Romero et al., "Neural Morphological Effects of Long-Term Implantation of the Self-Sizing Spiral Cuff Nerve Electrode", *Medical & Biological Engineering & Computing*, 2001, vol. 39, pp. 90-100.
Sahin et al., "Spiral Nerve Cuff Electrode for Recordings of Respiratory Output", *The Spiral Nerve Cuff Electrode*, 1997 American Physiological.Society, pp. 317-322.
Schmidt, R.A., "Applications of Neurostimulation in Urology", 1988; 7:585-92.
Spinelli, M., et al., "A New Minimally Invasive Procedure for Pudendal Nerve Stimulation to Treat Neurogenic Bladder: Description of the Method and Preliminary Data", Neurourol and Urodyn. 2005: 24:305-309.
Starbuck, D. L., Mortimer, J.T., Sheally, C.N., Reswick, J.B. (1966) An implantable electrodes system for nerve stimulation, Proc 19$^{th}$ Ann. Conf. on Eng. In Med. and Biol. 8:38.
Starbuck, D.L. (1965) Myo-electric control of paralyzed muscles. IEEE Transactions on Biomedical Engineering 12(3):169-172, Jul.-Oct.
Sundin, T., et al., "Detrusor inhibition induced from mechanical stimulation of the anal region and from electrical stimulation of pudendal nerve afferents," Investigative Urology, 5, 374-8 (1974).
Sweeney, et al., "A Nerve Cuff Technique for Selective Excitation of Peripheral Nerve Trunk Regions", *IEEE Transactions on Biomedical Engineering*, vol. 37, No. 7, Jul. 1990.
Talaat, M., "Afferent Impulses in the Nerves Supplying the Urinary Bladder", Journal of Physiology 1937: 89-1-13.
Tanagho, E.A., et al. "Electrical Stimulation in the Clinical Management of the Neurogenic Bladder", J. Urol. 1988; 140:1331-1339.
Tyler, et al., "Chronic Response of the Rat Sciatic Nerve to the Flat Interface Nerve Electrode", *Annals of Biomedical Engineering*, vol. 31, pp. 633-642, 2003.
Veraart, C., Grill, W.M., Mortimer, J.T., (1993) Selective control of muscle activation with a multipolar nerve cuff electrode, IEEE Trans. Biomed. Engineering 40:640-653.
Vodusek, D.B., et al. "Detrusor Inhibition Induced by Stimulation of Pudendal Nerve Afferents", Neuroul and Urodyn., 1986; 5:381-389.
Wheeler, et al., "Bladder inhibition by penile nerve stimulation in spinal cord injury patients", The Journal of Urology, 147(1), 100-3 (1992).
Wheeler, et al., "Management of Incontinent SCI patients with Penile Stimulation; Preliminary Results," J. Am. Paraplegia Soc. Apr. 1994: 17(2):55-9.
www.devicelink.com, MPMN, May 2004, Liquid-Crystal Polymer Meets the Challenges of RF Power Packaging; The plastic air-cavity packages are hermetically sealed using a proprietary process, Susan Wallace.
www.foster-miller.com, Project Examples, Packaging for Implantable Electronics, Foster-Miller, Inc. Feb. 15, 2006.
www.machinedesign.texterity.com, Vacuum-Formed Films for Fit and Function, High-Performance Films can Replace Injection-Molded Plastics When Space is at a Premium, David Midgley, Welch Fluorocarbon Inc., Dover, NH Oct. 7, 2004.
Yang, C., et al., "Peripheral Distribution of the Human Dorsal Nerve of the Penis", J. Urol 1998; 159(6):1912-6, discussion 1916.
PCT Search Report dated Feb. 2, 2009 for PCT/US08/081762 (7 pgs.).
Reply to Written Opinion dated Nov. 13, 2008 for PCT/US07/014396 (13 pgs.).
Notification of Transmission of IPRP dated Jun. 26, 2009 for PCT/US07/014396 (7 pgs.).
Notification of Transmittal of the International Search Report and Written Opinion dated Jul. 18, 2008 for PCT/US08/002540 (10 pgs.).
PCT Written Opinion dated Feb. 2, 2009 for PCT/US08/081762 (10 pgs.).
Office Action dated Jun. 26, 2009 for U.S. Appl. No. 11/824,931 (11 pgs.).
Restriction Requirement dated Sep. 9, 2009 for U.S. Appl. No. 11/517,213 (7 pgs.).
Response dated Oct. 8, 2009 for U.S. Appl. No. 11/517,213 (1 pg.).
Restriction Requirement dated Jul. 25, 2008 for U.S. Appl. No. 11/712,379 (10 pgs.).
Response dated Oct. 27, 2008 for U.S. Appl. No. 11/712,379 (1 pg.).
Office Action dated Dec. 22, 2008 for U.S. Appl. No. 11/712,379 (9 pgs.).
Responsive Amendment dated Apr. 22, 2009 for U.S. Appl. No. 11/712,379 (11 pgs.).
Office Action dated Jul. 6, 2009 for U.S. Appl. No. 11/712,379 (12 pgs.).
Responsive Amendment dated Sep. 8, 2009 for U.S. Appl. No. 11/712,379 (8 pgs.).
Advisory Action dated Sep. 30, 2009 for U.S. Appl. No. 11/712,379 (3 pgs.).
Office Action dated Jan. 22, 2010 for U.S. Appl. No. 11/517,213 (16 pgs.).
Responsive Amendment dated Apr. 22, 2010 for U.S. Appl. No. 11/517,213 (21 pgs.).
Office Action dated Jun. 25, 2010 for U.S. Appl. No. 11/517,213 (7 pgs.).
Responsive Amendment dated Aug. 25, 2010 for U.S. Appl. No. 11/517,213 (17 pgs.).
Office Action dated Dec. 9, 2010 for U.S. Appl. No. 11/517,213, (16 pgs).
Responsive Amendment dated Mar. 9, 2011 for U.S. Appl. No. 11/517,213, (17 pgs).
MCP7381/2/3/4 Datasheet, "Advance Single or Dual Cell Lithium-Ion/Lithium-Polymer Charge Management Controllers," Microchip Technology Inc., 2004 (24 pgs.).
Office Action dated Apr. 20, 2011 for U.S. Appl. No. 11/517,213, (18 pgs).
Response dated Jun. 20, 2011 for U.S. Appl. No. 11/517,213, (18 pgs).
Supplemental European Search Report dated Apr. 21, 2011 for European Application No. 07777090.7 (6 pgs.).
Office Action dated Jul. 14, 2011 for U.S. Appl. No. 11/974,279, (17 pgs).
Responsive Amendement dated Oct. 14, 2011 for U.S. Appl. No. 11/794,279, (20 pgs.).
Final Office Action dated Oct. 13, 2011 for U.S. Appl. No. 12/825,089, (11 pgs.).
Responsive Amendment dated Dec. 13, 2011 for U.S. Appl. No. 12/825,089, (14 pgs.).
Respose to Communication dated May 10, 2011 for European Application No. 07777090.7 (2029219) filed Nov. 21, 2011, (37 pgs).
Examination Report dated Feb. 9, 2012 for European Patent Application No. 07777090.7-2305, 5 pgs.).

(56) References Cited

OTHER PUBLICATIONS

Supplemental Search Report dated Aug. 8, 2012 for European Application No. 08 72 61202, (8 pgs.).

Response dated Jun. 11, 2012 for European Application No. 07777090.7, (8 pgs.).

Response to Office Action dated Mar. 30, 2015, from U.S. Appl. No. 11/517,213, filed Jun. 30, 2015, 12 pp.

Decision on Appeal from U.S. Appl. No. 11/517,213, dated Dec. 12, 2014, 21 pp.

Office Action from U.S. Appl. No. 12/825,089, dated Dec. 5, 2013, 12 pp.

Notice of Allowance from U.S. Appl. No. 11/517,213, mailed Nov. 30, 2015, 5 pp.

Decision on Appeal from U.S. Appl. No. 11/517,170, dated Sep. 15, 2014, 18 pp.

Notice of Allowance from U.S. Appl. No. 11/517,170, dated Apr. 13, 2015, 9 pp.

Final Office Action from U.S. Appl. No. 11/517,213, dated Sep. 18, 2015, 6 pp.

Notice of Allowance from U.S. Appl. No. 11/517,170, mailed Aug. 3, 2015, 9 pp.

Final Office Action from U.S. Appl. No. 15/063,073, dated Aug. 12, 2016, 8 pp.

\* cited by examiner

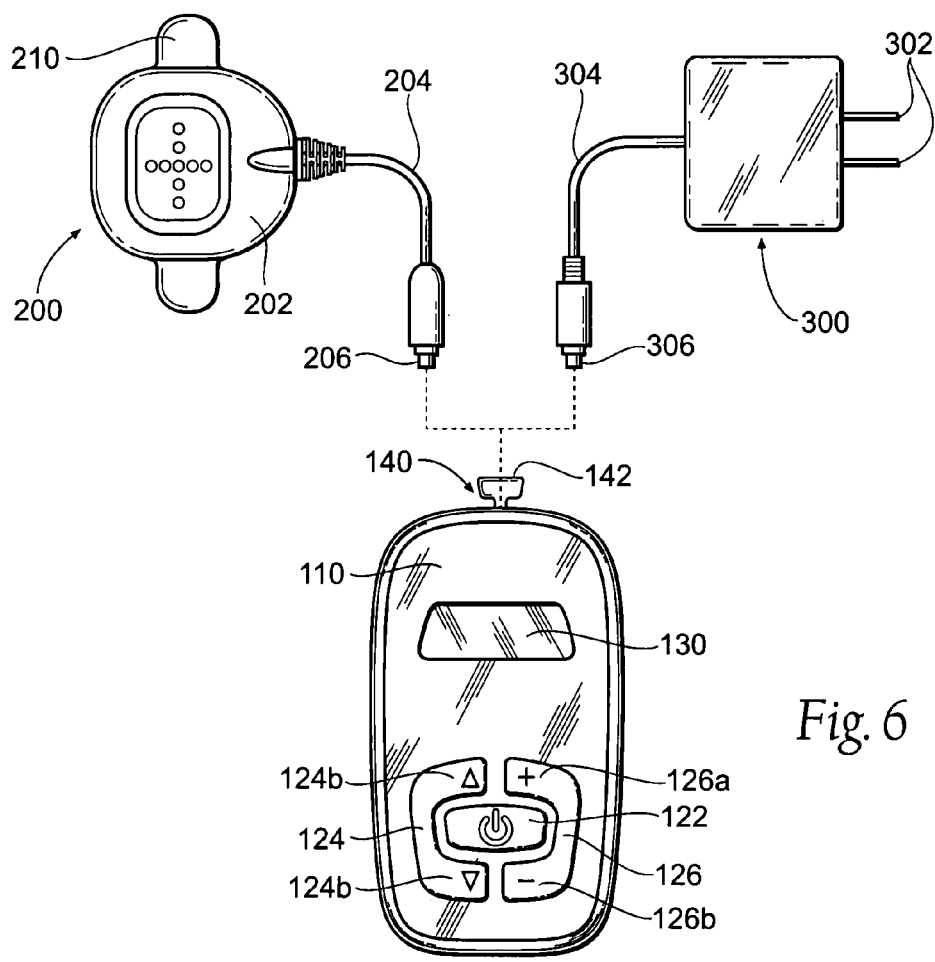
Fig. 6
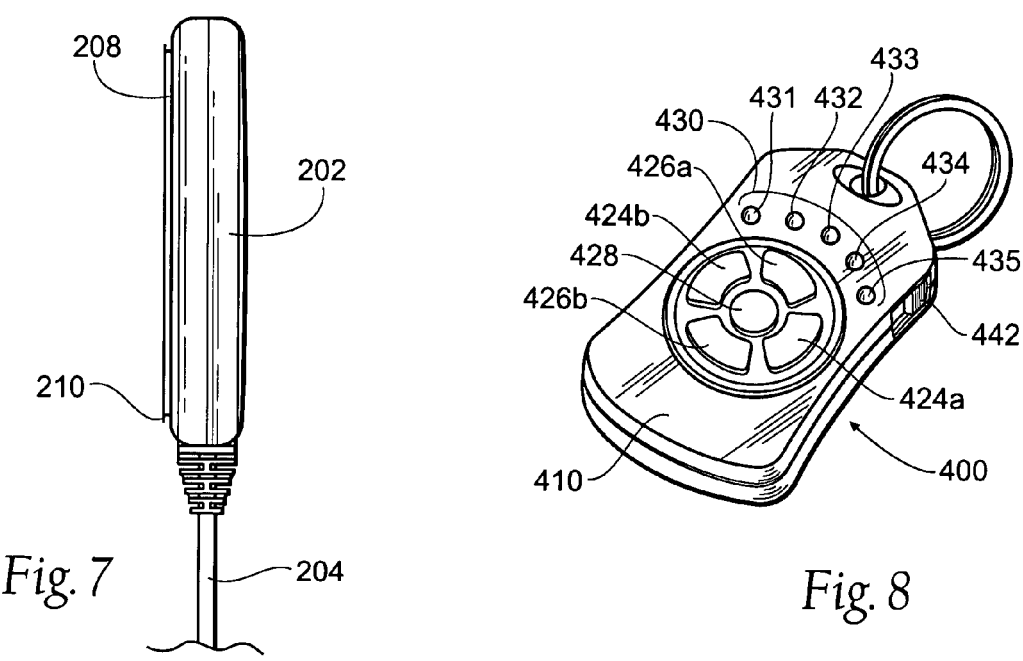
Fig. 7
Fig. 8

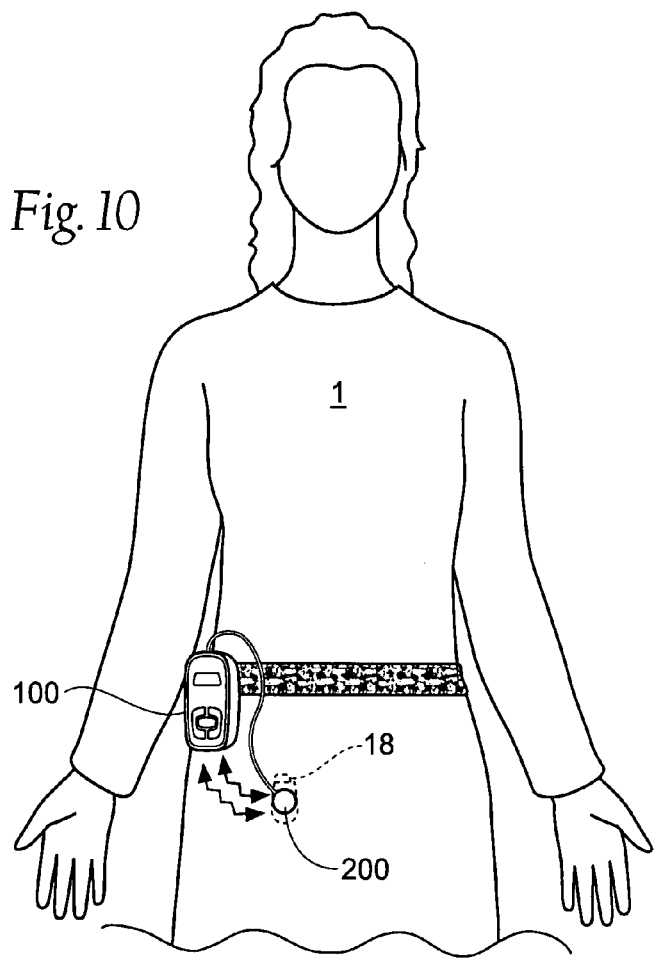
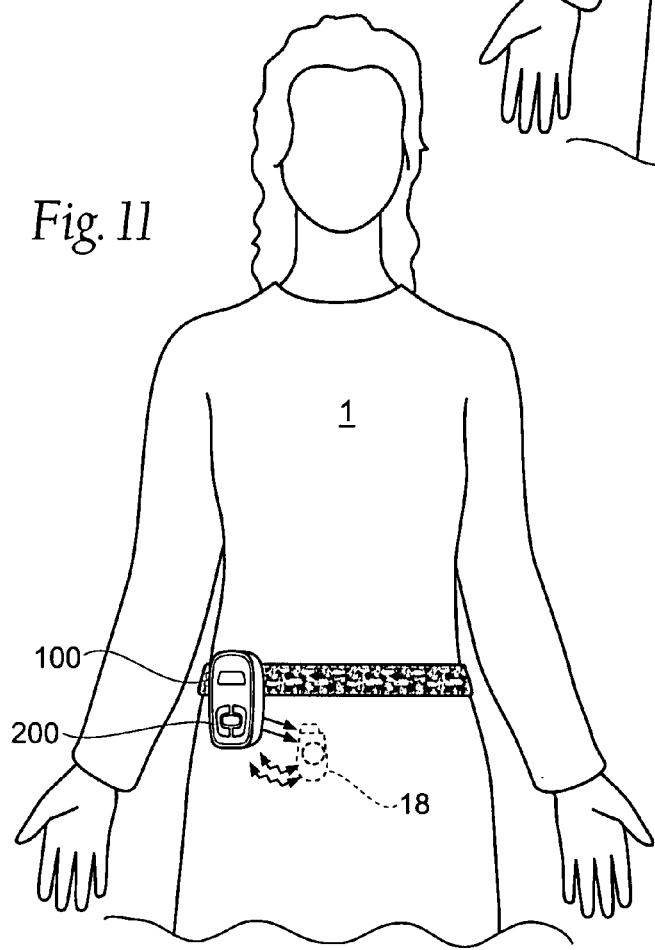

SYSTEMS AND METHODS FOR PATIENT CONTROL OF STIMULATION SYSTEMS

RELATED APPLICATIONS

This application is a continuation-in-part of co-pending U.S. patent application Ser. No. 11/516,890, filed 7 Sep. 2006, and entitled "Implantable Pulse Generator Systems and Methods for Providing Functional and/or Therapeutic Stimulation of Muscles and/or Nerves and/or Central Nervous System Tissue," which claims the benefit of U.S. Provisional Patent Application Ser. No. 60/801,003, filed 17 May 2006, and entitled "Implantable Pulse Generator for Providing Functional and/or Therapeutic Stimulation of Muscle and/or Nerves and/or Central Nervous System Tissue."

BACKGROUND

The invention relates generally to systems and methods for control of electronic devices. More specifically, the present invention relates to systems and methods for the programming and recharging of medical devices, and especially neurostimulating devices, either by the patient receiving treatment from the device or by a caregiver.

Medical devices are commonly used today to treat patients suffering from various ailments, including by way of example, pain, incontinence, movement disorders such as epilepsy, Parkinson's disease, and spasticity. Additional stimulation therapies appear promising to treat a variety of other medical conditions, including physiological, psychological, and emotional conditions. As the number of stimulation therapies increases, so do the demands placed on these medical devices.

Known stimulation devices, such as cardiac pacemakers, tachyarrhythmia control devices, drug delivery devices, and nerve stimulators, provide treatment therapy to various portions of the body. While the present invention may be used with various medical devices, by way of example and illustration, an implantable pulse generator (IPG) device will be discussed to illustrate the advantages of the invention. In the case of providing electrical stimulation to a patient, an IPG is implanted within the body. The IPG is coupled to one or more electrodes to deliver electrical stimulation to select portions of the patient's body. Neuromuscular stimulation (the electrical excitation of nerves and/or muscle to directly elicit the contraction of muscles), neuromodulation stimulation (the electrical excitation of nerves, often afferent nerves, to indirectly affect the stability or performance of a physiological system) and brain stimulation (the stimulation of cerebral or other central nervous system tissue) can provide functional and/or therapeutic outcomes.

There exist both external and implantable devices for providing beneficial results in diverse therapeutic and functional restorations indications. The operation of these devices typically includes the use of an electrode placed either on the external surface of the skin, a vaginal or anal electrode, or a surgically implanted electrode. Implantable medical devices may be programmable and/or rechargeable, and the devices may log data, which are representative of the operating characteristics over a length of time.

Implantable devices have provided an improvement in the portability of neurological stimulation devices, but there remains the need for continued improvement in the control of such devices either by the patient into whom a device is implanted or by a caregiver. Medical devices are often controlled using microprocessors with resident operating system software. This operating system software may be further broken down into subgroups including system software and application software. The system software controls the operation of the medical device while the application software interacts with the system software to instruct the system software on what actions to take to control the medical device based upon the actual application of the medical device.

As the diverse therapeutic and functional uses of stimulators increase and become more complex, system software having a versatile interface is needed to play an increasingly important role. This interface allows the system software to remain generally consistent based upon the particular medical device, and allows the application software to vary greatly depending upon the particular application. As long as the application software is written so it can interact with the interface, and in turn the system software, the particular medical device can be used in a wide variety of applications with only changes to application specific software. This allows a platform device to be manufactured in large, more cost effective quantities, with application specific customization occurring at a later time.

While handheld programmers are generally known in the art, the programmers are generally controlled only by a treating physician or clinician. Therefore, to modify device settings, an office visit is normally required. Such office visits are especially inefficient where the required adjustment of the medical device is such that the patient or caregiver could accomplish the adjustment with minimal training. Therefore, there exist many gaps in handheld controller devices and methods for the controlling and recharging of medical devices, especially those of the implanted type, either by the patient receiving treatment from the device or by a caregiver.

Furthermore, although it is generally known to use rechargeable power supplies or batteries in implanted medical devices, methods heretofore employed to recharge the implanted devices most often required the patient to remain relatively motionless or in a relaxed position. Since the recharging process for the devices can be lengthy, the limitations in patient movement could hinder the patient's lifestyle, especially if recharging was required during the patient's waking hours. For example, a patient using a prior art method of recharge may be prevented from running simple errands because of the virtual or physical tether to prior art recharging apparatus.

Therefore, the field of medical treatment by implantable medical devices would benefit from a portable apparatus that provides a patient or caregiver the ability to recharge and alter the parameters of an implanted medical device, while at the same time allowing the patient substantially unobstructed mobility.

SUMMARY

The present invention comprises a portable apparatus and associated method that provides a patient or caregiver the ability to recharge and alter the parameters of an implanted medical device, while at the same time allowing the patient substantially unobstructed mobility.

BRIEF DESCRIPTION OF THE DRAWINGS

FIG. 6 is a front elevation view of the first embodiment of FIG. 1, further including charging coil and power supply accessories.

FIG. 7 is a side elevation view of the charging coil of FIG. 6.

FIG. 8 is a perspective view of a second embodiment of a handheld controller.

FIG. 10 is a first illustration of use of the embodiment of FIG. 1.

FIG. 11 is an illustration of use of an alternative embodiment of the handheld controller.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
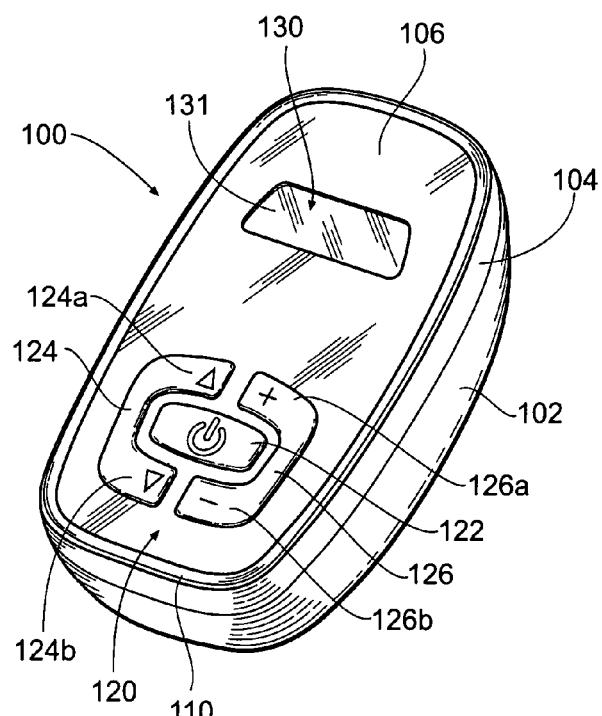
FIG. 1 is a perspective view of a first embodiment of a handheld controller.

Turning now to the Figures, FIG. 1 is a perspective view of a first embodiment of a handheld patient stimulator controller 100. The controller 100 comprises a base 102, a bezel 104, and a lens 106, all of which, when assembled, form a protective shell 110, which generally contains electronic circuitry. The base 102 is generally a hollow, bowl-shaped component having a bottom 102a and a continuous wall 102b extending therefrom. The bezel 104 has a first surface 104a, which is desirably adapted to be placed and secured in a mating relationship to the base wall 102b. The bezel 104 may be secured to the base 102 by way of adhesive or even a locking physical structure, but more desirably by way of threaded fasteners. The bezel 104 also has a second surface 104b, which may be recessed, thereby providing a surface to which the lens 106 may anchor. Both the base 102 and the bezel 104 are desirably molded to any desirable shape using injection molding of a suitable material such as Lustran® acrylonitrile-butadiene-styrene (ABS) 348 resin, or a polycarbonate ABS material that would allow thinner component construction and enhanced shock absorption. The lens 106 has a first surface 106a, which is adapted to rest against the bezel second surface 104b. To maintain proper positioning of the lens 106, the lens first surface 106a may be provided with an adhesive. The lens 106 is desirably formed by injection molding of a material that can offer desired optical clarity. The shell 110 is desirably appropriately sized to easily fit in a user's hand. For example, a desirable shell 110 may be about the size of other small personal electronic devices that may be about 7 centimeters long, about 4 centimeters wide, and about 1 centimeter thick.

Disposed on or in the shell 110 are two interfaces; a user input interface 120 and a user output, or feedback, interface 130. The user input interface 120 desirably comprises a plurality of buttons; a power button 122, a mode select pad 124, and a parameter adjustment pad 126. The power button 122 is desirably a push button to power the controller 100 on and off. The mode select pad 124 desirably provides two buttons; a mode up button 124a and a mode down button 124b. The adjustment pad 126 also desirably provides two buttons; an increase button 126a and a decrease button 126b. Furthermore, a select button (not shown) may be included as a part of the user input interface 120, similar to the other buttons. The select button could provide a means of affirmative indication by the user that a setting of the device 100 is acceptable. Desirably, all buttons of the user input interface 120 interface with at least one electronic component contained in the controller 100. The buttons are desirably injection molded silicone rubber.

In addition to the user input interface 120, the controller 100 comprises a user output interface 130. The depicted controller 100 is shown with a liquid crystal display (LCD) screen 131 as the user output interface 130. The function of the user output interface 130 is to provide some visual feedback such as a status or operating mode of the controller 100, a status of a medical device, or a preview of programming parameters to be transferred to the medical device. By utilizing the LCD screen 131, specific diagrammatic figures and parameter values may be displayed. Additional user output display components may include other visual indicators such as simple light-emitting diodes (LEDs), or aural indicators such as piezo buzzers or variable audio tones.

Figure 2:
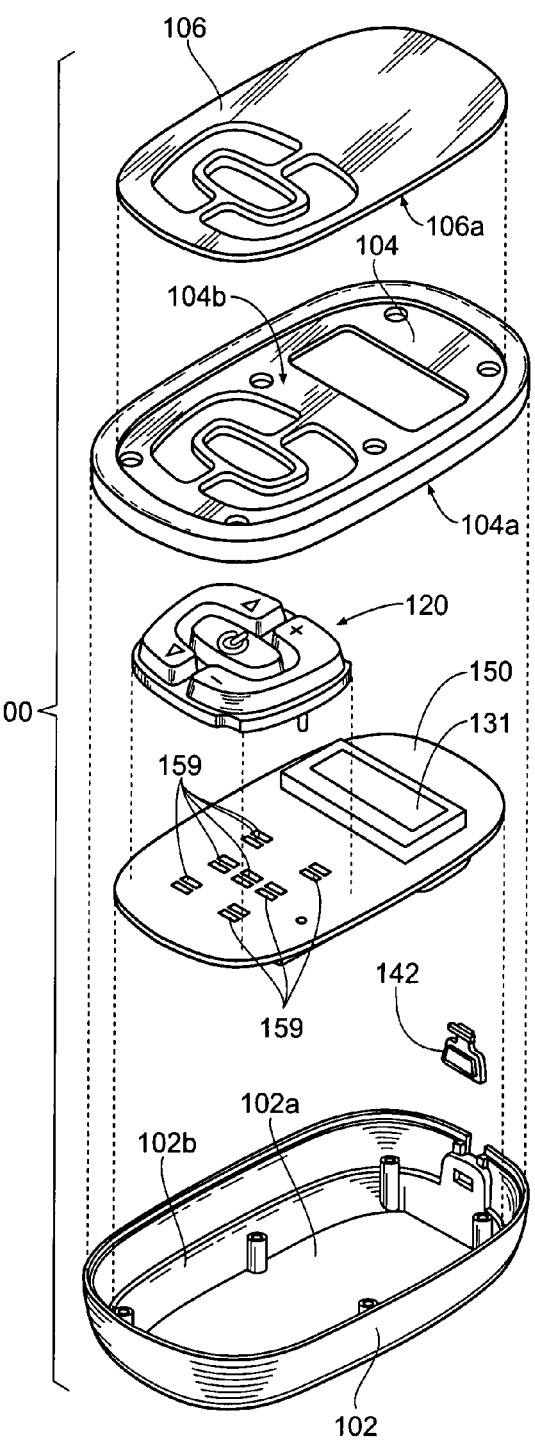
FIG. 2 is a perspective exploded view primarily showing the main structural components of the first embodiment of FIG. 1.

FIG. 2 is a general exploded view of the controller 100 of FIG. 1, showing the basic assembly of the controller 100, and further showing a printed circuit assembly (PCA) 150 on which electronic circuitry contained in the shell 110 may be supported and interconnected. Instead of using only a single PCA 150, a plurality of PCAs may be used.

Figure 3:
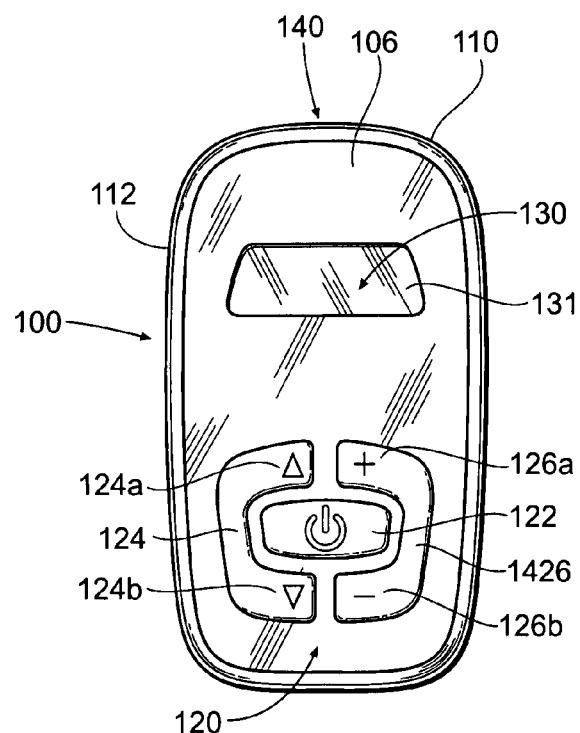
FIG. 3 is a front elevation view of the first embodiment of FIG. 1.
Figure 4:
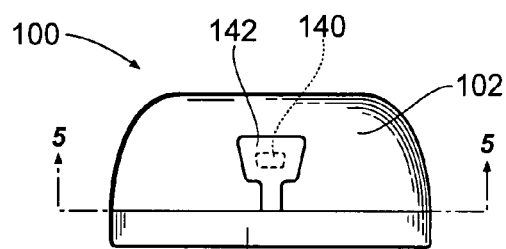
FIG. 4 is a top plan view of the first embodiment of FIG. 1.

Referring also to FIGS. 3 and 4, which simply show different views of the embodiment of FIG. 1, the controller 100 may be supplied with at least one receptacle or port 140 for receiving plugs from external accessories or components. The one or more receptacles 140 are electrically coupled to the appropriate electronic components. While a plurality of receptacles 140 could be provided, it is desirable to have only a single port 140 to allow the connection of only a single accessory at any given time. Where a single port 140 is meant to provide an interface for a variety of accessories, the port 140 and the accessory plugs may be keyed differently such that, by providing electrical contact surfaces in different locations in connection with the port 140, the controller 100 is able to distinguish between connected accessories. The receptacle 140 is desirably covered with a protective gasket 142, which prevents the receptacle 140 from being contaminated with dust or other particulates, and may protect the receptacle 140 from exposure to moisture. The gasket 142 is desirably injection molded out of any suitable material such as Santoprene® thermoplastic elastomer, available from Advanced Elastomer Systems, LP. The gasket 142 is held in place desirably by the clamping force holding the base 102 and bezel 104 together.

Figure 5:
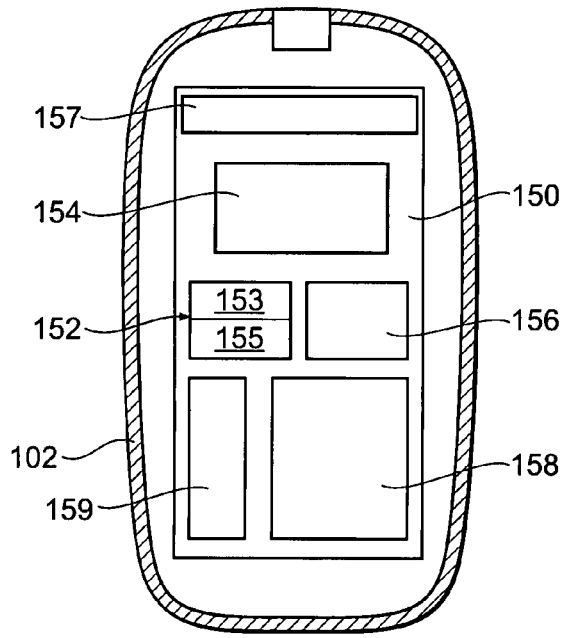
FIG. 5 is a cross-section view of the first embodiment taken along line 5-5 of FIG. 4.

FIG. 5 diagrammatically depicts electrical components arranged, in no particular order, on the PCA 150, shown in FIG. 2, which is housed in the shell 110. By way of electrical components, the controller 100 desirably includes a power supply 152, a programmable microcontroller 154, an accessory controller 156, a wireless telemetry module 158, electrical connectors 157, and user interface components 159, all in operative electrical connection.

The power supply 152 may be a rechargeable battery 153 and associated charging and indication circuitry 155. The rechargeable battery 153 may be recharged when connected to a power source, such as when the controller 100 is connected by a power adaptor 300 to a wall outlet, or is docked on a docking station (not shown). Addressing safety concerns, the controller 100 desirably may not be used to recharge an IPG 18 while the controller 100, itself, is being recharged through the power adaptor 300. The charging and indication circuitry 155 provides to the microcontroller 154 periodic updates of the status of the battery 153 and charging thereof. The battery 153 is desirably secured in the shell so that it cannot be removed easily, so as to discourage accidental disposal by users.

The programmable microcontroller 154 provides the general intelligence of the controller 100, and desirably includes a predetermined amount of memory to hold desirable software; however, the memory may also be supplied as a separate component. The microcontroller 154 generally controls the operation of the user output interface 130, the accessory controller 156 and the wireless telemetry module 158, all depending upon the mode of operation as selected by the user input interface 120 or some other source.

The accessory controller 156 is desirably a slave to the microcontroller 154 and provides the requisite electronic control of an accessory, such as a charging coil 200. The accessory controller 156 is activated by the microcontroller 154 when the associated accessory is detected as being coupled to the controller 100 through the receptacle 140. A single accessory controller 156 may supply the requisite control of a plurality of accessories, or, alternatively, a plurality of accessory controllers 156 may be supplied.

The telemetry module 158 may incorporate a suitable wireless telemetry transceiver chip set that can operate in the Medical Implant Communications Service (MICS) band (402 MHz to 405 MHz) or other very high frequency (VHF) or ultra high frequency (UHF) low power, unlicensed bands. A wireless telemetry link established between the controller 100 and an implanted medical device is especially useful in motor control applications where a user issues a command to an IPG to produce muscle contractions to achieve a functional goal (e.g., to stimulate ankle flexion to aid in the gait of an individual after a stroke). The wireless telemetry is desirably non-inductive radio frequency telemetry. Therefore, communications between the controller 100 and the IPG 18 desirably does not require a coil, or other component, taped or placed on the skin over the IPG 18, thereby enhancing user maneuverability and allowing communications desirably up to a distance of six feet between the controller 100 and the IPG 18. A suitable transceiver chip that may be used for half duplex wireless communications is the AMIS-52100, available from AMI Semiconductor, Pocatello, Id. This transceiver chip is designed specifically for applications using the MICS band and the MICS European counter-part, the Ultra Low Power-Active Medical Implant (ULP-AMI) band.

The electrical connectors 157 on the PCA 150 may provide operative electrical interconnectivity between the PCA 150 and various electrical components, such as the LCD 131, the receptacle 140, other PCAs, or even a standardized test setup, such as a Joint Test Action Group (JTAG) interface.

User interface components 159 convert user input to electrical signals to be used by the controller 100 and further convert electrical signals into indicators that are to be sensed by a user. As user interface components 160 to the user input interface 130, it is desirable to provide a plurality of split electrical contacts 162 to indicate when a user has communicated through the user input interface 120. The contacts 162 are electrically coupled to the microcontroller 154 to indicate such user activity. An electrically conductive surface is provided on a bottom side of the plurality of buttons on the user input interface 120, so as to connect both sides of the split contacts 162 when a button is depressed. Furthermore, the user interface components 160 further comprise the parts of the user output interface 130, such as the LCD 131.

FIG. 6 shows the controller 100 with external accessories, which may include a charge coil 200 and a power adaptor 300. The charge coil 200 desirably includes a predetermined construction comprising a housing 202, a coil cable 204, and a winding (not shown). The housing 202 is preferably formed to a desirable size out of a thermoplastic elastomer, such as Santoprene®. Such material aids in avoiding skin irritation that may arise as a result of long term exposure of a patient's skin to other materials. The winding can be of various construction but is desirably 150 to 250 turns, and more desirably 200 turns, of six electrically parallel strands of #36 enameled magnetic wire, or the like. Additionally, the charging coil outside diameter may be in a range of about 40 millimeters to about 70 millimeters, and desirably about 65 millimeters, although the diameter may vary. The thickness of the charging coil 104, as measured perpendicular to its mounting plane, is desirably significantly less than its diameter, e.g., about three millimeters to about eleven millimeters, so as to allow the coil 200 to be embedded or laminated in the housing 202 to facilitate placement on or near the skin. Such a construction allows for efficient power transfer and allows the charging coil 200 to maintain a safe operating temperature. As seen in FIG. 7, the coil 200 may be provided with an adhesive backing strip 208 to be removably coupled to a patient's skin. The strip 208 may be formed of closed-cell polyethylene foam, which would prevent overheating of the patient's skin adjacent the coil 200. The strip 208 has a skin-side adhesive surface, which is desirably protected by a release liner 210. The release liner 210 prevents contamination of the adhesive strip 208 prior to application on the skin. Returning to FIG. 6, the coil cable 204 comprises insulated electrical conductors providing at least two conductive paths, operatively coupled to the coil winding at one end and to an electrical plug 206 at the other end. Therefore, one electrical path provides electrical current to the coil 200 while the other path provides a return current to the controller 100. The electrical plug 206 serves as the electrical connection point between the controller receptacle 140 and the coil 200.

The power adaptor 300 provides the ability to recharge the controller battery 153. It comprises a power plug 302, converter 303, and a power cord 304. The power plug 302 is a conventional power plug adapted to cooperate with any standard wall outlet socket. The converter 303 receives alternating current power from the standard wall outlet socket, through the plug 302, and presents the appropriate voltage required by the battery charging circuitry 155 in the controller 100. The appropriate voltage is presented through the power cord 304, which includes a power connector 306, mateable with the controller receptacle 140. Alternating current power cords are generally known in the art, and many variations are available.

A second controller embodiment 400 is shown in FIG. 8. Like the first embodiment 100, this controller 400 has a user input interface 420 and a user output, or feedback, interface 430. The user input interface 420 comprises five buttons and a power switch 422. The power switch 422 of this embodiment 400 is desirably a single pole single throw slide switch 422 recessed below the outer surface of the controller shell 410. Once the controller 400 is powered on, manipulation of the electronics is accomplished through the five buttons on its face. The buttons are divided into two pairs surrounding a center button 428. One pair of buttons defines a mode pair 432,434 and the second pair of buttons defines an adjustment pair 442,444. The center button. 428 is desirably a general purpose "OK" or "Select" button. All buttons and switches of the user input interface 420, are operationally coupled to at least some of the electronics contained in the controller 400.

The user output interface 430 is provided desirably in the form of a plurality of light emitting diodes (LEDs) 431-435. The LEDs have different display functionality depending upon the incident operating state of the electronic components within the controller 400. Similar to the first embodiment 100, the second embodiment 400 contains various electronic components (not shown). The second embodiment 400 desirably includes a non-rechargeable battery as its power supply and does not include an accessory controller. Therefore, the primary function of a reduced size controller, such as the second embodiment 400, is the adjustment of stimulation parameters and monitoring of IPG status rather than recharging the IPG battery.

It is to be appreciated that the controller 100 may take on any convenient shape, such as a ring on a finger, a watch on a wrist, or an attachment to a belt, for example. It may also be desirable to separate the functions of the controller 100 into a charger and a patient controller.

Figure 9:
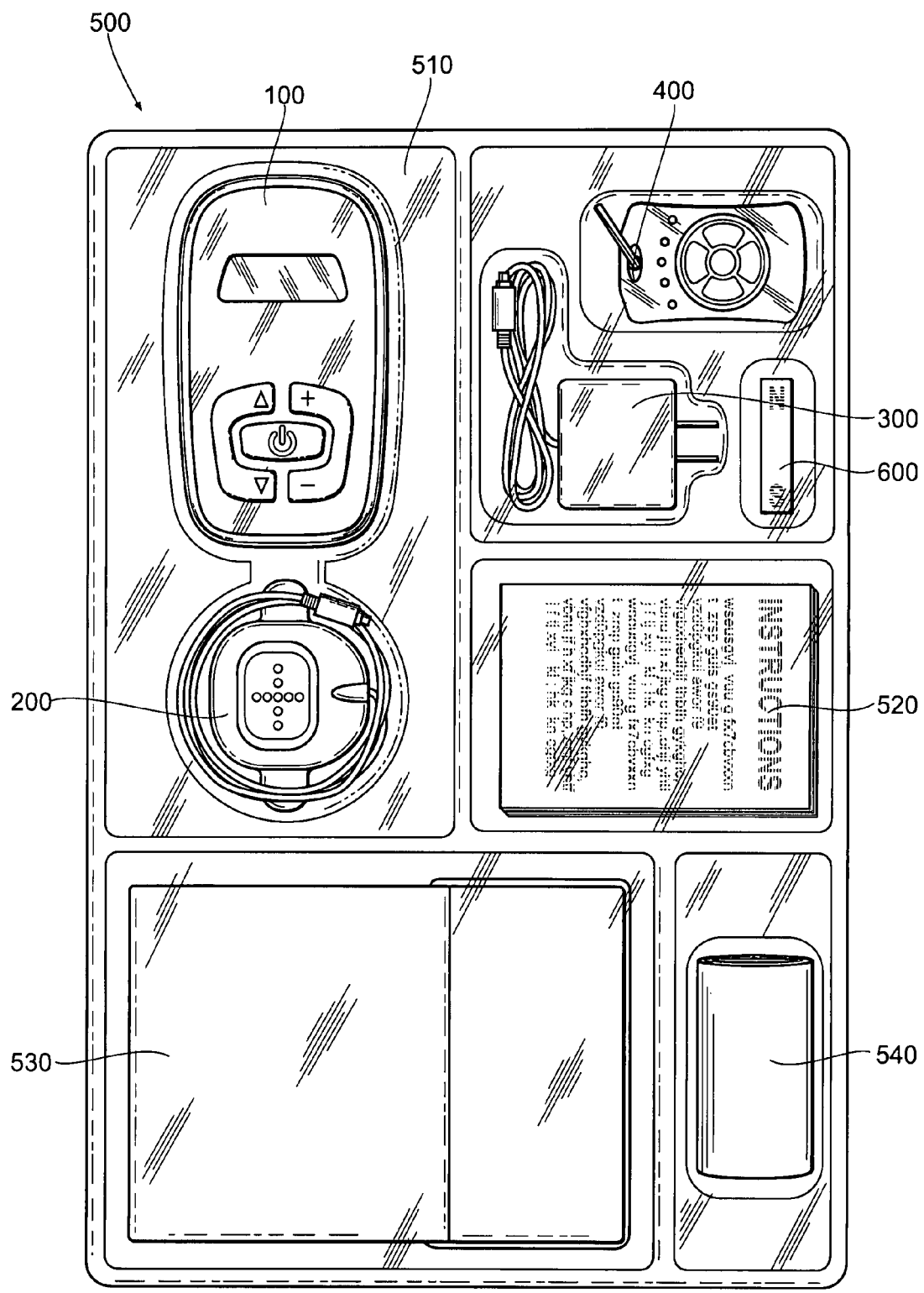
FIG. 9 is a top plan view of a controller kit.

FIG. 9 depicts a controller kit 500 that may be provided in a packaging 510 and including a controller 100, a charging coil 200, a power adaptor 300, a second controller 400, a set of user instructions 520, a carrying case 530, record media 540, and a remote device 600. The remote device 600 may be a simple magnet that enables transcutaneous activation and deactivation of an IPG 18 including magnetic controls, such as a reed switch. The record media 540 may be paper or self-adhesive labels to be used by a patient or physician in conjunction with record keeping. The packaging 520 can be made from any method now known in the art such as plastic molding. The kit 500 may also be provided without the remote device 600, the second controller 400, the instructions 520, the carrying case 530 or the record media 540.

Turning to FIGS. 9-13, methods of operation of the described controller embodiments are explained herein. While the controller 100 may be used with a variety of devices, the working example herein will concern use in conjunction with an implantable pulse generator (IPG) 18. The IPG 18 desirably incorporates a rechargeable battery that can be recharged transcutaneously and a non-inductive radio frequency (RF) wireless telemetry system to enable transcutaneous communication. With the use of the controller 100, a patient may control certain predefined parameters of the implantable pulse generator within a predefined limited range. The parameters may include the operating modes/states, increasing/decreasing or optimizing stimulus patterns, or providing open or closed loop feedback from an external sensor or control source. Wireless telemetry also desirably allows the user to interrogate the implantable pulse generator 18 as to the status of its internal battery. The full ranges within which these parameters may be adjusted by the user are desirably controlled, adjusted, and limited by a clinician, so the user may not be allowed the full range of possible adjustments. That is, while a given IPG parameter may be adjustable by a clinician over a number of settings, it is desirable that a patient have access to modify the parameters over only a limited range, less than the number of settings than a clinician has access to. Therefore, a clinician may develop a desirable treatment regimen for a given patient's condition and program the limited parameter range according to the treatment regimen.

The rechargeable battery of the IPG 18 may be recharged by the application of a transcutaneous low frequency RF magnetic field applied by a charging coil 200 mounted on a patient's skin or clothing and placed over or near the IPG 18. The transcutaneous RF magnetic field may have a frequency range of about 30 Khz to about 300 Khz. To begin charging, the charging coil 200 is placed proximate the IPG 18 and connected by the coil cable 204 to the controller 100, and electrically coupled to the accessory controller 156 through the controller receptacle 140. The coil 200 may be held in place manually, but it is desirable that the coil 200 be removably fastened to the skin by way of the adhesive backing strip (208 in FIG. 7), or inserted into a pouch (not shown) having an adhesive backing strip, the pouch being removably coupled to the skin. Alternatively, the pouch (not shown) could be coupled to a belt or other supporting structure, which is then worn by the user so as to properly position the coil 200.

FIG. 11 portrays an alternative application, in which it is anticipated that a controller 100 may include an internal charging coil 200. A user 1 would then support or wear the controller 100, which includes the internal charging coil 200, over the IPG 18 to recharge the IPG 18 battery.

The controller 100 and the IPG 18, as shown in FIGS. 9 and 10 may also use wireless telemetry to provide a "smart charge" feature to indicate that charging is occurring and to make corrections to allow for optimal recharging and protect against overcharging. During a battery recharge period, the smart charge causes the controller 100 to issue commands to the IPG 18 at predetermined intervals, e.g., thirty seconds, to instruct the IPG 18 to confirm that the generated RF magnetic field is being received and is adequate for recharging the rechargeable battery. If the controller 100 does not receive a response from the IPG 18 to confirm that the generated RF magnetic field is being received, the controller 100 may stop generating the RF magnetic field.

During the battery recharge period, the IPG 18 may transmit status information, such as an indication of the battery charge status and an indication of the magnitude of power recovered by the receive coil 200, back to the controller 100.

Based on the magnitude of the power recovered, the smart charge allows the controller 100 to automatically adjust up or down the magnitude of the magnetic field and/or to instruct the user to reposition the charging coil 200 based on the status information to allow optimal recharging of the battery of the IPG 18 while minimizing unnecessary power consumption by the controller 100 and power dissipation in the IPG 18 (through circuit losses and/or through absorption by the implantable pulse generator case 20 and other components). The magnitude of the RF magnetic field 100 may be automatically adjusted up to about 300 percent or more of the initial magnitude of the RF magnetic field and adjusted down until the controller 100 stops generating the RF magnetic field. Adjustment of the RF magnetic field 100 may also result from sensing a desirable temperature on the skin side of the charging coil 200. That is, the magnitude may be increased or decreased if a sensed temperature is low enough or too high, respectively. Temperature sensing may be achieved by any general way known in the art, such as a thermistor or thermocouple.

The instructions to the user to reposition the charging coil 200 may be a visual instruction, such as a bar graph on the controller 100, or a display on the controller 100 showing relative positions of the charging coil 200 and the IPG 18, or an audio instruction, such as a varying tone to indicate relative position, or a combination of instructions.

In addition to a rechargeable battery, the IPG 18 may incorporate wireless telemetry for a variety of functions, such as receipt and transmission of stimulus parameters and settings, receiving requests for and transmitting battery and operating status, allowing user control of the implantable pulse generator 18, and for assisting in the control of the RF magnetic field generated by the controller 100. To enable reliable wireless communications, each IPG may have a unique signature that limits communication to only certain dedicated controllers. This signature could be a serial number that is stored in the IPG in non-volatile electronic memory or by other means. While an interface device or controller used by a clinician or physician may be configured for use with many patients and many IPGs by configuring the clinical programmer with various desired serial numbers, such broad functionality is not generally desirable for patients or caregivers.

The controller 100 is desirably the master of all wireless communications between it and an IPG 18. Therefore, to begin a wireless communication, the controller 100 generates and sends a wireless telemetry communication to an IPG 18, the communication including the IPG's unique serial number and data elements that indicate the communication is a command from an external controller 100. Only the IPG 18 having the unique serial number responds to the communication from the controller 100. The communication response includes elements that indicate the communication is a response to a command from an external controller 100, and that the communication is not a command from a different external controller.

Communications protocols include appropriate received message integrity testing and message acknowledgment handshaking to assure the necessary accuracy and completeness of every message. Some operations (such as reprogramming or changing stimulus parameters) require rigorous message accuracy testing and acknowledgement. Other operations, such as a single user command value in a string of many consecutive values, might require less rigorous checking and no acknowledgement or a more loosely coupled acknowledgement. Integrity testing may be accomplished through the use of parity bits in the communication messages or even the use of a cyclic redundancy check (CRC) algorithm. Implementation of parity and CRC algorithms are generally known in the communications art.

The timing with which an IPG enables its transceiver to search for RF telemetry from an external controller may be precisely controlled (using a time base established by a quartz crystal) at a relatively low rate, e.g., the IPG may look for commands from the external controller for about two milliseconds at a rate of two (2) Hz or less. This equates to a monitoring interval of about ½ second or less. It is to be appreciated that an IPG's enabled transceiver rate and the monitoring rate may vary faster or slower depending on the application. This precise timing allows the external controller to synchronize its next command with the time that the IPG will be listening for commands. This, in turn, allows commands issued within a short time (seconds to minutes) of the last command to be captured and acted upon without having to 'broadcast' an idle or pause signal for a full received monitoring interval before actually issuing the command in order to know that the IPG will have enabled its receiver and be ready to receive the command. Similarly, the communications sequence may be configured to have the external controller issue commands in synchronization with the IPG listening for commands. Similarly, the command set implemented may be selected to minimize the number of messages necessary and the length of each message consistent with the appropriate level of error detection and message integrity monitoring. It is to be appreciated that the monitoring rate and level of message integrity monitoring may vary faster or slower depending on the application, and may vary over time within a given application.

The wireless telemetry communications may also be used in conjunction with the IPG battery charging function. It is especially useful in cases where two implant charger controllers 100 could be erroneously swapped, or where two or more IPGs 18 may be within wireless telemetry range of each other. For example, when two users live in the same home, a first IPG 18 could communicate with its controller 100 even when the charging coil 200 is erroneously positioned over another IPG 18. The controller 100 is configured to communicate and charge a specifically identified IPG, or a target IPG, which is identified by the unique signature or serial number. If the target IPG is wirelessly communicating with a controller 100 that is erroneously positioned, the target IPG communicates with the controller 100 to increase the magnitude of the RF magnetic field. This communication may continue until the magnitude of the RF magnetic field is at its maximum.

In order to stop a controller 100 from attempting to charge the incorrect IPG 18, the controller 100 may periodically decrease the magnitude of the RF magnetic field and then wirelessly communicate with the target IPG 18 to determine whether the target IPG 18 sensed the decrease in the magnitude. If the charging coil 200 is erroneously positioned over an IPG other than the target IPG 18, the target IPG 18 will not sense the decrease and will indicate to the controller 100 that it did not sense the decrease. The controller 100 will then restore the original RF magnetic field strength and retry the reduced RF magnetic field test. Multiple failures of the test may cause the controller 100 to suspend charging and notify the user 1 of the error. Similarly, should the IPG 18 not recover usable power from the RF magnetic field after a few minutes, the controller 100 will suspend charging and notify the user 1 of the error.

Figure 15:
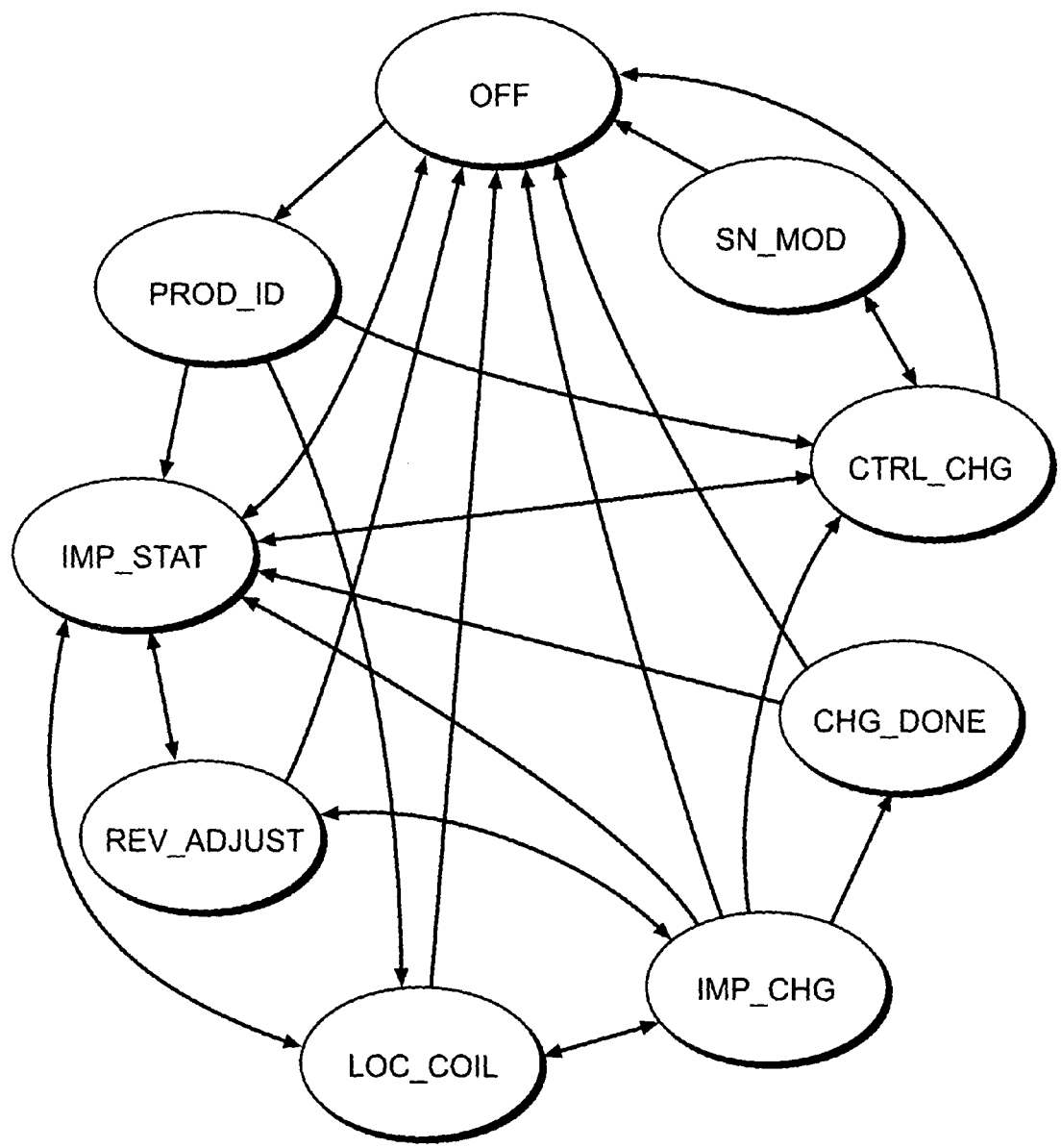
FIG. 15 is a diagrammatic illustration of an embodiment of software flow of software utilized by a microcontroller in the handheld controller.
Figure 15A:
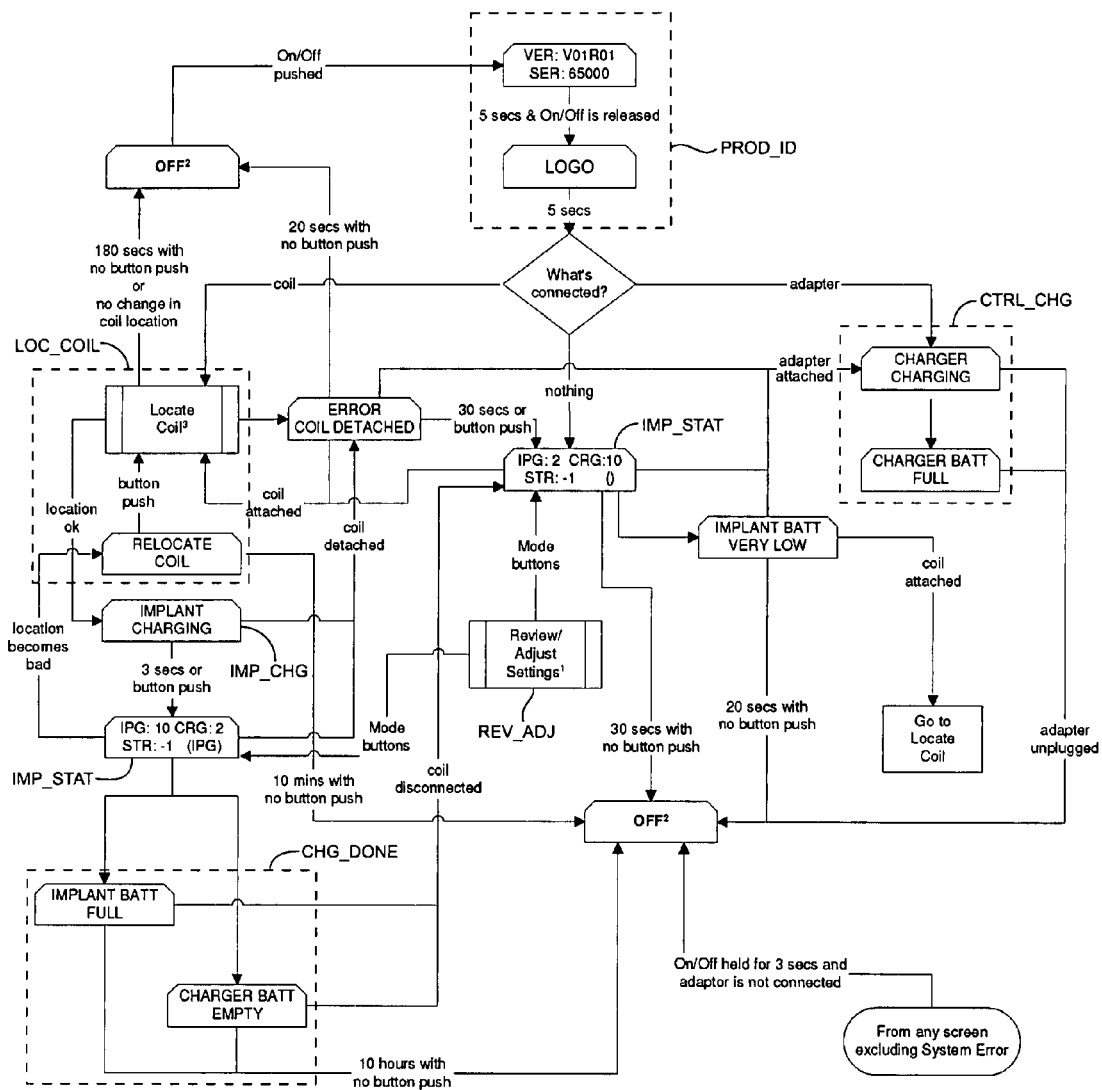
FIGS. 15A-E provide more specific embodiments of an implementation of the software flow embodiment of FIG. 15.
Figure 15B:
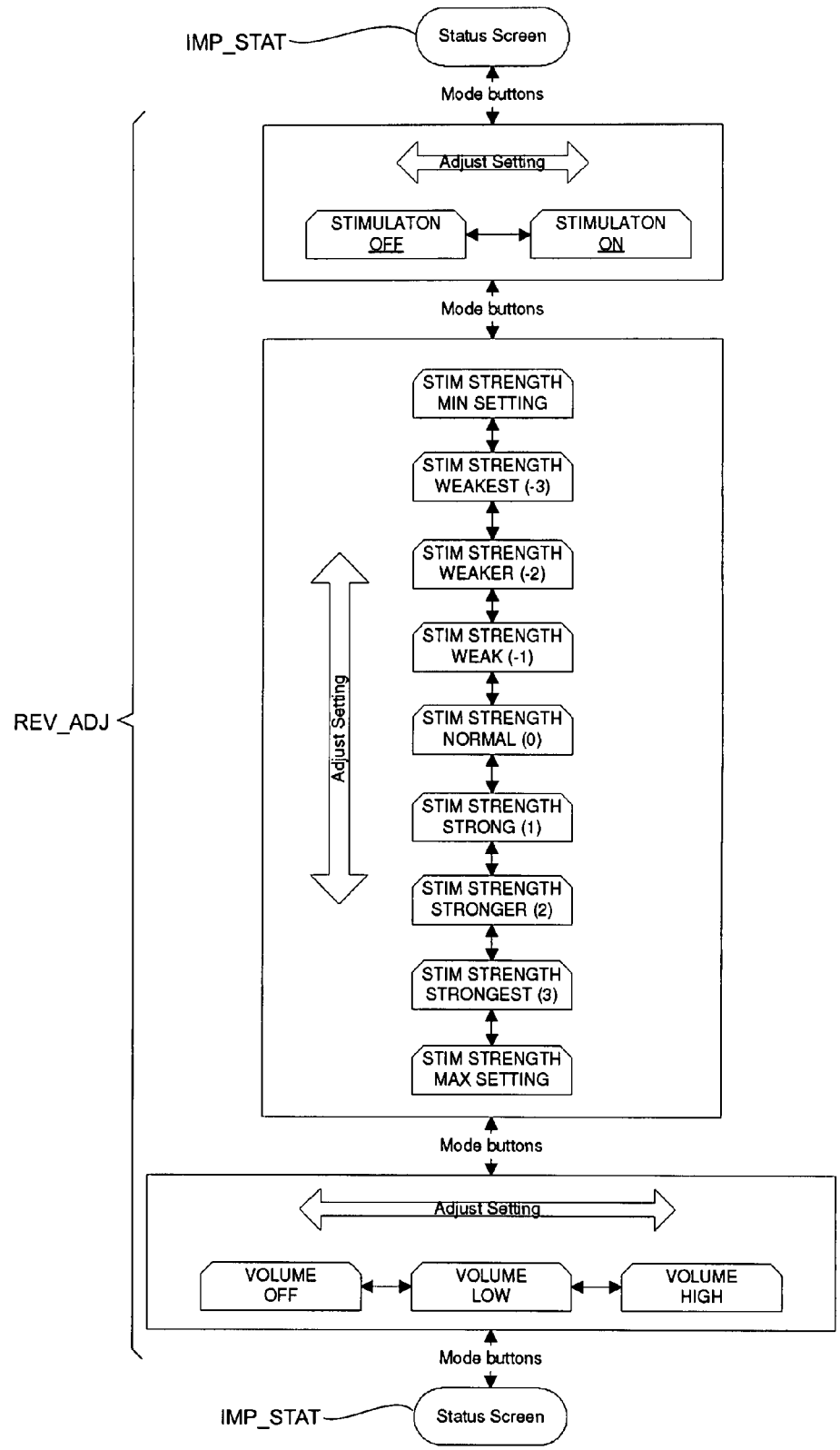
Figure 15C:
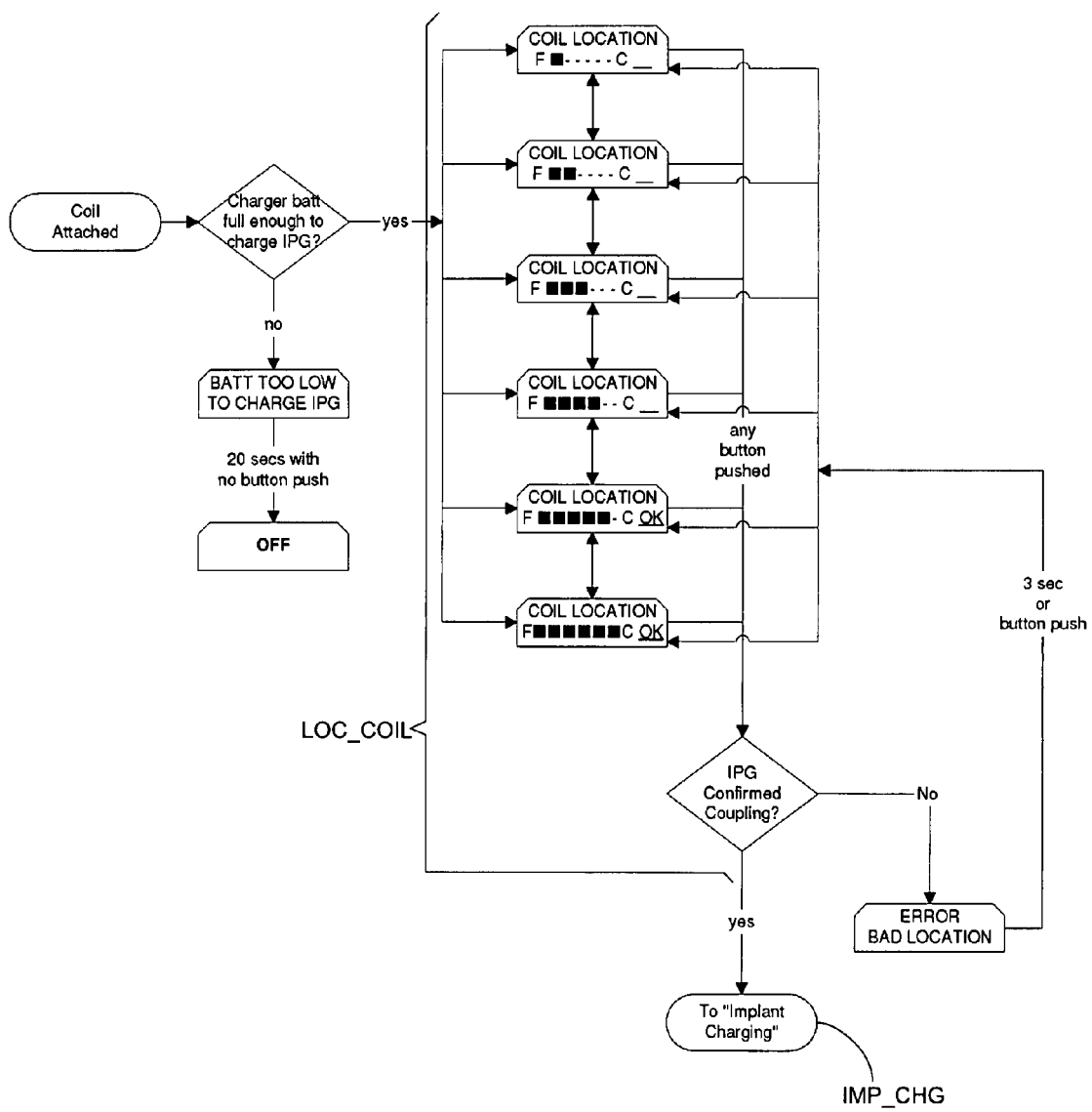

Operation of the system can perhaps best be described with a working example explaining different operating modes of the controller 100 incorporating an LCD screen 131. Generally, the controller 100 operates so as to provide an interface between an IPG and a patient in which the device is implanted, or a caregiver thereof. The controller 100 provides the ability for the patient to recharge the IPG, query the IPG regarding its present settings, to adjust the IPG settings, and to recharge the controller 100. As shown in the flowchart in FIG. 15, an embodiment of the controller 100 desirably has nine different operating modes: OFF, PROD_ID, IMP_STAT, REV_ADJ, LOC_COIL, IMP_CHG, CHG_DONE, CTRL_CHG, and SN_MOD. For reasons explained in more detail below, only the first eight modes are desirably available to the patient or caregiver, the ninth mode being controlled by a supervising physician. It is to be understood that not all of the modes of operation are mutually exclusive and, therefore, some modes may be functional at overlapping times. FIGS. 15A-E provide an exemplary software flow.

OFF: The controller 100 may enter the OFF mode from any other mode by a mere passage of time, or the user may affirmatively enter the OFF mode from any operating mode.

While the controller 100 is in the OFF mode, controller power consumption is minimal and the user output interface 130 is desirably deactivated. Optionally, however, a simple "heartbeat" or other nominal indication may be shown on the output interface 130 to represent some state of the controller.

From the OFF mode, the controller 100 may enter the PROD_ID mode or the IMP_STAT mode. To enter the PROD_ID mode, there are desirably two methods of removing the controller 100 from the OFF mode. First, a user could depress the power button 122. While depression of other buttons on the controller 100 could possibly turn the device 100 on, to minimize accidental activation, it is desirable that only one button, the power button 122, activate the device 100. Second, a user could supply power to the controller 100 through a power adaptor 300. Therefore, if the controller 100 entered the OFF mode without error, when the controller 100 wakes from the OFF mode, it desirably enters the PROD_ID mode. If, on the other hand, the controller 100 was in the IMP_STAT mode and had a fatal system error occur prior to entering the OFF mode, the controller 100, upon leaving the OFF mode, desirably enters the IMP_STAT mode with an error indicator displayed, as shown in one embodiment in FIG. 15E.

PROD_ID: The controller 100 may enter the PROD_ID, or product identification, mode from the OFF mode.

Upon entering the PROD_ID mode, a temporary indicator such as an informational screen, or "splash screen," may be displayed, including information such as device information, manufacturer, software revision, date, time, etc. This screen or plurality of indicators remains active for a predetermined amount of time before entering the next mode.

From the PROD_ID mode, the controller 100 may enter the following modes: IMP_STAT, LOC_COIL, or CTRL_CHG. The mode following the PROD_ID mode depends on whether an accessory is connected, and, if so, which accessory is connected. If no accessory is connected, the mode switches from PROD_ID to IMP_STAT. If the power adaptor 300 is connected through the controller receptacle 140, the next mode is CTRL_CHG. Finally, if the charge coil 200 is connected through the controller receptacle 140, the next mode is LOC_COIL.

IMP_STAT: The controller 100 may enter the IMP_STAT, or implant status, mode from the following modes: OFF, PROD_ID, REV_ADJ, LOC_COIL, IMP_CHG, or CTRL_CHG. If the controller 100 entered the OFF state during an error condition, powering on the controller 100 preferably places it in the IMP_STAT mode with an indication of the error state. Assuming no accessory is connected as the controller 100 is exiting the PROD_ID mode, the controller 100 enters the IMP_STAT mode. From the REV_ADJ mode, IMP_STAT is entered by a mere passage of one of the following: a predetermined amount of time after REV_ADJ mode was entered; a predetermined amount of time after any parameter modifications are made; or, a predetermined amount of time after a predetermined combination of the mode buttons 124a, 124b are depressed. From the LOC_COIL mode or from the IMP_CHG mode, the controller 100 may enter the IMP_STAT mode where a charge coil 200 is disconnected and fails to be reconnected within a predetermined amount of time. From the CTRL_CHG mode, the controller 100 enters the IMP_STAT mode if the power adaptor 300 is disconnected from the controller 100. The predetermined amounts of time may be anything greater than zero seconds, but is desirably between 3 and 30 seconds.

The IMP_STAT mode may be a desirable base operating mode on top of which other modes may run. Upon entering the IMP_STAT mode, information is displayed to the user. If the cause of entering this mode is a disconnected charge coil 200, it is desirable to display an indication of the charge coil 200 disconnect that has occurred. Furthermore, through the user output interface 130, it is desirable to convey three pieces of information. One item is the battery charge status of the controller 100. The other two items depend on whether successful wireless communications can be established with the IPG 18. If communications are not established, a message to that effect is desirably displayed. If communications can be established, the battery charge status of the IPG 18 is displayed, along with a present parameter setting, such as a stimulus intensity level. Rather than the three listed pieces of information, or in addition to that information, other status indicators or user commands could also be displayed through the user output interface 130.

From the IMP_STAT mode, the controller may enter the following modes: OFF, REV_ADJ, LOC_COIL, and CTRL_CHG. The user may do nothing, or may depress the power button 122, for a predetermined period of time, and the controller 100 desirably proceeds to the OFF mode. The user may depress a button on the mode select pad 124 to enter the REV_ADJ mode. To enter the LOC_COIL mode, the user may connect a charge coil 200 to the controller receptacle 140. Finally, the user may connect a power adaptor 300 to the controller receptacle 140 and to an active wall socket to enter the CTRL_CHG mode.

REV_ADJ: The controller 100 may enter the REV_ADJ, or review and adjust settings, mode from the following modes: IMP_STAT or IMP_CHG. If the user is in either of these modes and depresses the mode select button 124, the controller 100 will switch into the REV_ADJ mode.

Figure 12:
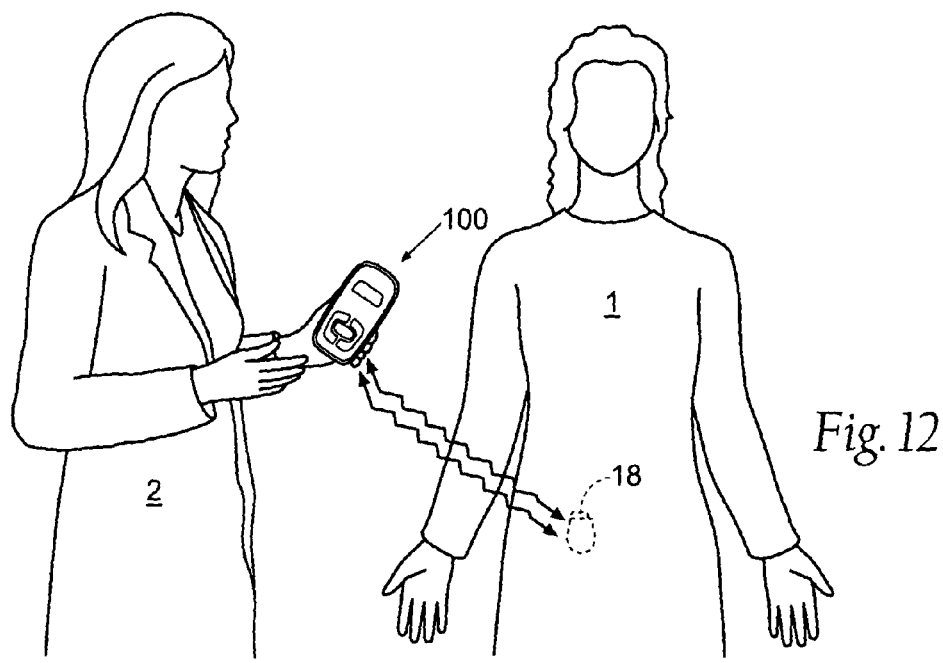
FIG. 12 is a second illustration of use of the embodiment of FIG. 1.
Figure 15D:
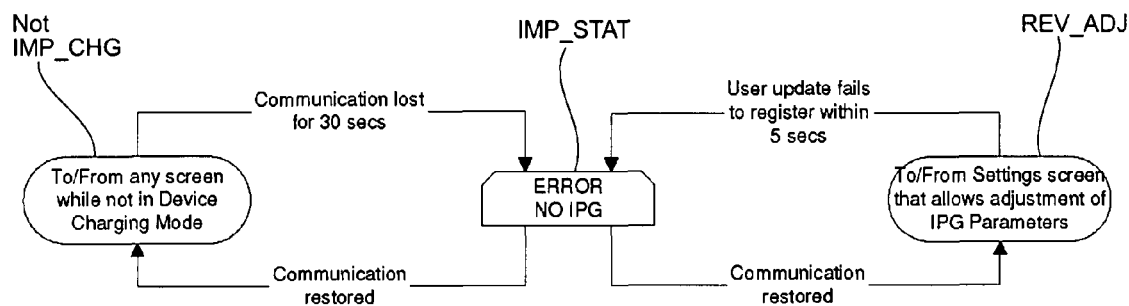
Figure 15E:
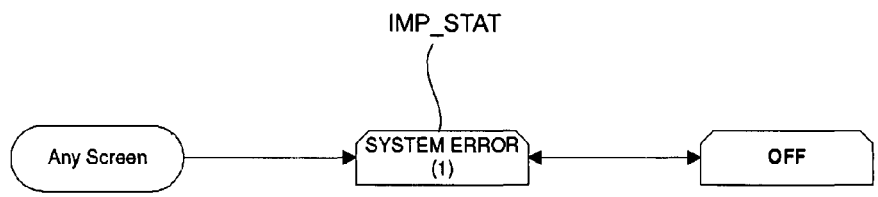

In this mode, the user has the option to adjust various settings both of the controller 100 and of the IPG 18. While the REV_ADJ mode is active, the mode select button 124 allows the user to scroll between parameters. For example, the user may wish to alter the volume of an audio indicator from the controller 100. The user simply navigates to the volume parameter using the mode select button 124 and then changes the volume setting by using the parameter adjustment button 126. Other parameters may be adjusted, such as IPG stimulation intensity and IPG stimulation activation. The stimulation intensity is generally only a vague, abstract number to the patient. That is, the patient's physician will dictate the various stimulation profiles available to the patient through the use of the controller 100 in combination with the IPG 18. The patient will only see, desirably, a numerical indicator of which profile is activated and may possibly reference a correlative list of what those numerical indicators actually mean with regards to the technical settings of the IPG 18, such as pulse width, amplitude and frequency of the stimulation. Therefore, as seen in FIG. 12, the physician 2 may establish a "normal" or baseline stimulation level and the patient 1 may be able to adjust from the baseline plus or minus three steps, however those steps may be defined by the physician 2. In the REV_ADJ mode, after the user has selected the desired value for the adjusted parameter, the controller 100 will indicate to the user that the parameter has been selected and is being transmitted to the IPG 18. Such indication could be accomplished a variety of ways, such as specific iconic or textual displays, or even a simple change in the appearance of the screen, such as a flashing screen. Upon communication of the changed parameters to the IPG 18, or a predetermined amount of time thereafter, the controller 100 exits the REV_ADJ mode and returns to the IMP_STAT mode. The controller 100 may also exit the REV_ADJ mode after a predetermined input from the user input interface 120. An embodiment of the flow through the REV_ADJ mode can be seen in FIG. 15B. Furthermore, should communications between the controller 100 and the IPG 18 be lost, an error message may be communicated through the user output interface 130, as shown in FIG. 15D. The controller 100 may then attempt to restore communications with the IPG 18.

From the REV_ADJ mode, the controller 100 may enter all of the modes from which the mode may have been entered: IMP_STAT or IMP_CHG. The mode to which the controller 100 proceeds depends on which mode it was in before the REV_ADJ mode was entered. It may return to the mode from which it came by the mere passage of a predetermined period of inactivity, by the depression of the power button 122.

LOC_COIL: The controller 100 may enter the LOC_COIL, or locate charging coil, mode from the following modes: PROD_ID, IMP_STAT or IMP_CHG. From the PROD_ID mode, if a charging coil 200 is coupled to the controller 100, it enters the LOC_COIL mode automatically. From the IMP_STAT mode, rather than plug in the power adaptor 300 to the receptacle, the user could connect the charging coil 200 to the controller 100 causing it to enter the LOC_COIL mode. From the IMP_CHG mode, if the inductive coupling between the charge coil 200 and the IPG 18 becomes ineffective for purposes of charging, the controller 100 may be forced into the LOC_COIL mode. An implementation of the LOC_COIL mode can be seen in FIG. 15C.

Once in the LOC_COIL mode, a visual indication is displayed and the controller 100 emits a locating tone. The screen 131 displays a graphical indication of the quality of the charging coil 200 placement proximate the IPG 18, and further includes an indicator, graphical or textual, that appears when the quality of the charging coil 200 placement is adequate to allow normal charging of the IPG battery. Desirably, depression of either the mode button 124 or the parameter adjustment button 126 has no effect on the controller 100 during the time it is locating the proper placement of the coil 200. While maneuvering the coil 200 to locate the IPG 18, and throughout charging, the user is informed as to the quality and status of the charging progress, desirably visually and aurally. The user should especially be informed if the coil cable 204 becomes unplugged from the controller 100. Once the locating tone and/or display indicate that the coil 200 is in proper charging position, the user can begin charging by pressing the power button 122 to enter the IMP_CHG mode.

Two periods of inactivity will cause the controller 100 to at least imply repositioning of the coil 200 and/or the controller 100 to enable proper charging. First, if no wireless telemetry is successful for a predetermined period, the controller 100 warns the user of the lack of wireless communications with the IPG 18. Also, during coil location, periodic updates of coil location quality are calculated to provide adequate feedback to the user. However, if no wireless telemetry between the controller 100 and IPG 18 has been successful between a predetermined number of charge coil updates, the controller 100 will not indicate to the user that placement of the coil 200 is adequate for normal charging.

From the LOC_COIL mode, the controller 100 may enter the following modes: OFF, IMP_STAT and IMP_CHG. Inactivity on the part of the user for a predetermined time, three minutes for example, desirably causes the controller 100 to enter the OFF mode. The IMP_STAT mode is entered when a charge coil 200 is disconnected and fails to be reconnected within a predetermined amount of time. The IMP_CHG mode is entered when the user is satisfied with the positioning of the charging coil 200 and a triggering event occurs. The triggering event could be the depression of the power button 122 or the achievement of a predetermined charging power.

IMP_CHG: The controller may enter the IMP_CHG, or implant charging, mode from the following modes: LOC_COIL or REV_ADJ. Entry into this mode is caused by the occurrence of a triggering event. The triggering event may be a user-initiated event or an automatic reactive event. The user-initiated triggering event may be the depression of a button. The automatic reactive triggering event may be the mere passage of time, or even a sensed charge coil placement position.

The IMP_CHG mode desirably runs on top of the IMP_STAT mode. Once in the IMP_CHG, an indication is displayed on the LCD 131. While in this mode, the accessory controller 156 is driving the connected charging coil 200. The user output interface 130 indicates to the user the fact that charging is taking place, and may also indicate the status of the IPG battery charge. While in this mode, the user may also alter the settings of the IPG 18.

From the IMP_CHG mode, the controller 100 may enter the following modes of operation: OFF, IMP_STAT, REV_ADJ, LOC_COIL, CHG_DONE, or CTRL_CHG. The user may affirmatively cancel the charging process, in which case the controller 100 desirably enters the OFF mode or IMP_STAT mode. Depression of the mode select button 124 will cause the controller 100 to enter the REV_ADJ mode and provide indication to the user. The IMP_CHG mode completes when the IPG is fully charged or when the charge in the controller battery 153 is insufficient to continue adequate charging. When the IMP_CHG is not interrupted and allowed to proceed to completion, the controller 100 enters the CHG_DONE mode.

CHG_DONE: The controller 100 may enter the CHG_DONE, or charge done, mode from the IMP_CHG mode. The CHG_DONE mode is entered upon the occurrence of either a completely charged IPG 18 battery or upon the depletion of the controller battery 153 to a point where further implant charging would be ineffective. Desirably, although continued IPG charging may not be allowed, the depletion point would allow enough controller battery 153 charge to allow basic operation of the controller 100.

Status is communicated to the user through the user output interface 130. Desirably, no wireless communications occur between the controller 100 and the IPG 18 in this mode.

From the CHG_DONE mode, the controller 100 may proceed to the following modes: OFF or IMP_STAT. To place the controller 100 in the OFF mode from the CHG_DONE mode, the power button 122 is depressed for a predetermined period of time, or the controller could enter the OFF mode after a predetermined period of inactivity. Alternatively, if the charge coil is removed from the controller 100, it enters the IMP_STAT mode.

CTRL_CHG: The controller 100 may enter the CTRL_CHG mode from the following modes: PROD_ID, IMP_STAT or IMP_CHG. Entering from either PROD_ID or IMP_STAT mode occurs if power is supplied to the controller 100 by a connected power adaptor 300. The CTRL_CHG mode is entered from the IMP_CHG mode if the power adaptor 300 is coupled to the controller 100 within a predetermined amount of time from a disconnection of the charge coil 200. In this case, the unplugged coil 200 status may be communication through the user output interface 130 prior to entering the CTRL_CHG mode.

While in the CTRL_CHG mode, an indicator is displayed to the user through the user output interface 130. Where the user output interface 130 is an LCD 131, the indicator may be a separate screen, or simply an indicator displayed in combination with other screens. The indication provided may be that of the present controller battery 153 level and an indication that the battery is charging.

From the CTRL_CHG mode, the controller 100 may enter the following modes: OFF, IMP_STAT, or SN_MOD. The controller 100 enters the OFF mode if the power button 122 is depressed for a predetermined amount of time. The IMP_STAT mode is entered when the power adaptor 300 is disconnected from the controller 100, or when the controller battery 153 has been charged to a predetermined level. Finally, the controller 100 enters the SN_MOD mode when a certain combination of buttons is pressed.

SN_MOD: The controller 100 may enter the SN_MOD, or serial number modification, mode from the CTRL_CHG mode. The SN_MOD mode is entered by depressing a certain combination of buttons on the face of the controller 100 within a predetermined time. This mode is desirably not available to the patient or caregiver and is supplied primarily for maintenance of the device or review of the device settings by a supervising physician.

While in the SN_MOD mode, the physician may modify the serial number of the IPG with which the controller 100 should be communicating. This modification is accomplished by using the user input interface 120 and the user output interface 130.

From the SN_MOD mode, the controller 100 may enter either the OFF mode or the CTRL_CHG mode. To enter the OFF mode, the physician merely depresses the power button 122 for a predetermined period of time. If the power button 122 remains unpressed for a period of time, the controller 100 desirably returns to the CTRL_CHG mode from which it came to enter the SN_MOD mode.

Figure 14:
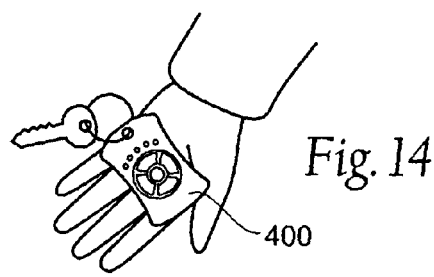
FIG. 14 is an illustration of use of the embodiment of FIG. 8.

Lastly, turning to a method of operation of the second embodiment 400 of the handheld controller, depicted in a user's hand in FIG. 14. With reference also to FIG. 8, a user turns the controller 400 on with the power switch 422 to communicate with an IPG 18. The user has the ability to switch modes using the mode up button 424a and the mode down button 424b. Desirable modes are (1) query present setting of IPG 18, (2) change stimulation setting of the IPG 18, (3) query battery level of the IPG 18, and (4) query battery level of the controller 400. When the controller 400 is activated by the power switch 422, the default mode is mode 1. The current mode is reflected by a predetermined patterned flash or constant light of the first LED 431. To query the present setting of the IPG 18, that is, to determine the present operating conditions of the IPG 18, the user presses the center button 428. The user feedback interface 430 then displays the result of the query. The LED corresponding to the current IPG setting will flash a predetermined number of times. The user output interface 430 will then display the mode it is in by maintaining an LED 431 lit.

To switch modes, the user 1 can scroll through the modes using the mode up button 424a or mode down button 424b. In mode 2, the user 1 can alter the stimulation profile with the profile up button 426a or profile down button 426b. When mode 2 is entered, the second LED 432 flashes a predetermined number times, and then the LED corresponding to the current IPG setting illuminates steady for a predetermined amount of time. While the present setting LED remains illuminated, the user 1 may propose a new IPG setting by using the profile up button 426a or profile down button 426b. The proposed setting LED flashes. For example, if the IPG 18 is currently set to stimulation profile 3, the third LED 433 will remain lit. If the user 1 hits the profile up button 426a, the fourth LED 434 will flash and the 3rd will remain lit. If, instead, the user 1 hits the profile down button 426b, the second LED 432 will flash and the third 433 will remain lit. If the user 1 wishes to maintain the current setting, the user 1 may hit the mode down button 424b, which serves as a "Back" function. If the user 1 wishes to continue to the new setting, indicated by the flashing LED, the user can hit the center button 428, which serves as an "OK" function.

Thus, when the IPG battery power is queried, the LEDs would illuminate from left to right indicating percentage of battery life remaining. Thus, to indicate 80% IPG battery life, the four leftmost LEDs would illuminate. To indicate 40% IPG battery life, the two leftmost LEDs would illuminate. The LEDs would switch off at the earlier of a predetermined time or the turning off of the power switch.

Figure 13:
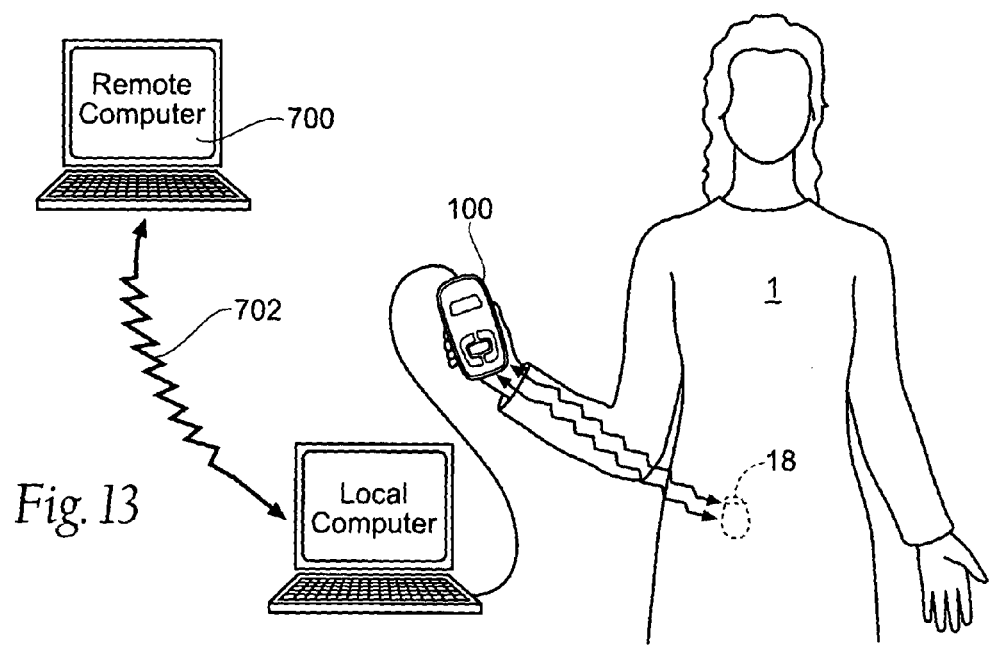
FIG. 13 is a third illustration of use of the embodiment of FIG. 1.

FIG. 13 contemplates control of the handheld controller 100 by a remote computer 700 over an operative connection 702. The operative connection 702 may be a packet switched connection established over a local area network connection, a wide area network connection, a wireless network connection, an internet connection. Alternatively, the operative connection 702 may be a more direct connection such as a serial RS-232 cable or USB cable. Over the operative connection 702, a supervising physician or other person with access may reprogram the handheld controller 100 or even query and modify parameters of an implanted medical device 18.

The foregoing is considered as illustrative only of the principles of the invention. Furthermore, since numerous modifications and changes will readily occur to those skilled in the art, it is not desired to limit the invention to the exact construction and operation shown and described.

We claim:

1. A portable controller for recharging and communicating with an implanted medical device, the controller comprising:
   a shell;
   a recharging module at least partially disposed in the shell, the recharging module configured to recharge a power supply of the implanted medical device; and
   a telemetry module at least partially disposed in the shell, the telemetry module configured to communicate via non-inductive wireless telemetry with the implanted medical device while the recharging module recharges the power supply of the implanted medical device, wherein the recharging module comprises a charging coil configured to generate a radio frequency magnetic field that transcutaneously recharges the power supply of the implanted medical device, and wherein the charging coil is at least partially disposed outside of the shell.

2. The portable controller of claim 1, wherein the recharging module is contained entirely in the shell.

3. The portable controller of claim 1, wherein the telemetry module is configured to communicate via non-inductive wireless telemetry with the implanted device over a distance of up to at least six feet.

4. The portable controller of claim 1, further comprising a port extending through the shell, the port in electrical communication with at least one of the recharging module or telemetry module.

5. The portable controller of claim 4, wherein the port is keyed.

6. The portable controller of claim 4, further comprising an accessory having a plug electrically coupled to the port.

7. The portable controller of claim 6, wherein the accessory plug is keyed.

8. The portable controller of claim 6, wherein the accessory is the recharging module.

9. The portable controller of claim 6, wherein the accessory is an alternating current (AC) power adaptor.

10. The portable controller of claim 1, further comprising a user interface for interaction with at least one of the recharge module or telemetry module, wherein the user interface comprises a user input interface.

11. The portable controller of claim 10, wherein the user input interface comprises a plurality of buttons.

12. The portable controller of claim 11, wherein the user input interface comprises no more than five buttons.

13. The portable controller of claim 10, wherein the user interface further comprises a user output interface.

14. The portable controller of claim 1, further comprising a user interface providing for interaction with at least one of the recharge module or telemetry module, wherein the user interface comprises a user output interface.

15. The portable controller of claim 14, wherein the user output interface comprises a liquid crystal display.

16. The portable controller of claim 14, wherein the user output interface comprises at least one light-emitting diode.

17. The portable controller of claim 14, wherein the user output interface comprises an audible tone.

18. The portable controller of claim 1, wherein the shell comprises:
a base having a bottom surface and sidewalls extending therefrom, the sidewalls having an upper edge defining a base perimeter;
a bezel secured to the base adjacent the base perimeter; and
a protective lens secured to the bezel.

19. The portable controller of claim 1, wherein the shell is about 7 centimeters long, about 4 centimeters wide and about 1 centimeter thick.

20. The portable controller of claim 1, wherein the telemetry module is configured to receive status information via non-inductive wireless telemetry from the implanted medical device while the recharging module recharges the power supply of the implanted medical device, wherein the portable controller at least one of adjusts the magnitude of the radio frequency magnetic field or instructs a user to reposition the charging coil based on the status information.

21. The portable controller of claim 1, wherein the wireless telemetry module communicates via non-inductive wireless telemetry in at least one of VHF or UHF frequency ranges.

22. A medical device controller comprising:
a shell;
a recharging module at least partially disposed in the shell, the recharging module configured to recharge a power supply of an implanted medical device; and
a telemetry module at least partially disposed in the shell, the telemetry module configured to communicate with the implanted medical device via non-inductive wireless telemetry, wherein the telemetry module is configured to communicate with the implanted medical device via non-inductive wireless telemetry while the recharging module recharges the power supply of the implanted medical device, wherein the recharging module comprises a charging coil configured to generate a radio frequency magnetic field that transcutaneously recharges the power supply of the implanted medical device, and wherein the charging coil is at least partially disposed outside of the shell.

23. The medical device controller of claim 22, wherein the telemetry module is configured to receive status information via non-inductive wireless telemetry from the implanted medical device while the recharging module recharges the power supply of the implanted medical device, wherein the portable controller at least one of adjusts the magnitude of the radio frequency magnetic field or instructs a user to reposition the charging coil based on the status information.

24. The medical device controller of claim 22, wherein the wireless telemetry module communicates via non-inductive wireless telemetry in at least one of VHF or UHF frequency ranges.

25. A portable controller for recharging and communicating with an implanted medical device, the controller comprising:
a shell;
a recharging module at least partially disposed in the shell, the recharging module configured to recharge a power supply of the implanted medical device; and
a telemetry module at least partially disposed in the shell, the telemetry module configured to communicate via non-inductive wireless telemetry with the implanted medical device while the recharging module recharges the power supply of the implanted medical device, and wherein the wireless telemetry module communicates via non-inductive wireless telemetry in at least one of VHF or UHF frequency ranges.

26. The portable controller of claim 25, wherein the recharging module is contained entirely in the shell.

27. The portable controller of claim 25, wherein the telemetry module is configured to communicate via the non-inductive wireless telemetry with the implanted medical device over a distance of up to at least six feet.

28. The portable controller of claim 25, further comprising a port extending through the shell, the port in electrical communication with at least one of the recharging module or the telemetry module.

29. The portable controller of claim 25, further comprising a user interface for interaction with at least one of the recharge module or the telemetry module, wherein the user interface comprises a user input interface.

30. The portable controller of claim 25, further comprising a user interface providing for interaction with at least one of the recharge module or the telemetry module, wherein the user interface comprises a user output interface.

31. The portable controller of claim 30, wherein the user output interface comprises a liquid crystal display.

32. The portable controller of claim 30, wherein the user output interface comprises at least one light-emitting diode.

33. The portable controller of claim 25, wherein the telemetry module is configured to receive status information via the non-inductive wireless telemetry from the implanted medical device while the recharging module recharges the power supply of the implanted medical device, wherein the portable controller at least one of adjusts the magnitude of the radio frequency magnetic field or instructs a user to reposition the charging coil based on the status information.

34. A medical device controller comprising:
   a shell;
   a recharging module at least partially disposed in the shell, the recharging module configured to recharge a power supply of an implanted medical device; and
   a telemetry module at least partially disposed in the shell, the telemetry module configured to communicate with the implanted medical device via non-inductive wireless telemetry, and wherein the wireless telemetry module communicates via non-inductive wireless telemetry in at least one of VHF or UHF frequency ranges.

35. The medical device of claim 34, wherein the recharging module is contained entirely in the shell.

36. The medical device of claims 34, wherein the telemetry module is configured to receive status information via the non-inductive wireless telemetry from the implanted medical device while the recharging module recharges the power supply of the implanted medical device, wherein the portable controller at least one of adjusts the magnitude of the radio frequency magnetic field or instructs a user to reposition the charging coil based on the status information.

* * * * *